United States Patent
Groenen et al.

(10) Patent No.: US 6,440,666 B1
(45) Date of Patent: Aug. 27, 2002

(54) SELECTION FOR DWARFISM IN POULTRY

(75) Inventors: Martinus Antonius Mathilda Groenen, Zetten; Gerardus Antonius Arnoldus Albers, Boxmeer, both of (NL)

(73) Assignee: Nutreco Nederland B.V. (NL)

( * ) Notice: Subject to any disclaimer, the term of this patent is extended or adjusted under 35 U.S.C. 154(b) by 0 days.

(21) Appl. No.: 09/341,444

(22) PCT Filed: Jan. 12, 1998

(86) PCT No.: PCT/NL98/00021
§ 371 (c)(1),
(2), (4) Date: Aug. 25, 1999

(87) PCT Pub. No.: WO98/30689
PCT Pub. Date: Jul. 16, 1998

(30) Foreign Application Priority Data

Jan. 10, 1997 (EP) .................................................. 9720070

(51) Int. Cl.$^7$ ................................................ C12Q 1/68
(52) U.S. Cl. .............................. 435/6; 435/5; 435/91.1; 435/91.2; 435/440; 435/455; 435/349; 536/24.31; 536/23.1; 514/44; 800/22
(58) Field of Search ................................ 435/440, 455, 435/349, 6, 91.1, 91.2, 5; 536/24.31, 23.1; 514/44; 800/22

(56) References Cited

PUBLICATIONS

Genomic Characterization of Human HMGIC, a Member of the Accessory Transcription Factor Family Found at Translocation Breakpoints in Lipomas; Ashar, H.R. et al; Genomics 31, 207–214 (1996).

Mutation responsible for the mouse pygmy phenotype in the developmentally regulated factor HMGI–C Zhou, X. et al. Nature, vol. 376 (Aug. 31, 1995) pp771–774.

The high mobility group I–C gene (HMGI–C): polymorphism and genetic localization Ishwad, C. et al Hum. Genet. (1997) 99: 103–105.

Living with bad architecture Lovell–Badge, R. Nature, vol. 376 (Aug. 31, 1995) pp725–726.

Genomic structure and expression of the murine Hmgi–c gene Zhou, X. et al. Nucleic Acids Research, 1996 vol. 24, No. 2 0; pp 4071–4077.

Production of functional chick liver HMG 2a protein in *Escherichia coli* Oka, T. et al; FEBS Letters 367 (1995) 49–52.

Decreased muscle cell proliferation in chicks with a deletion in the GH receptor gene Goddard, C. et al Journal of Molecular Endocrinology (1996) vol. 17 pp 67–78.

*Primary Examiner*—W. Gary Jones
*Assistant Examiner*—Janell E. Taylor
(74) *Attorney, Agent, or Firm*—Roberts & Merchanti, LLP

(57) ABSTRACT

The invention relates to a gene located on chromosome 1 in chickens, which in birds is involved in so called autosomal dwarfism. The most likely candidate gene has a homolog in mice and men and is called HMGI-c. The sequence of the cDNA and genomic DNA of the gene is provided, as well as uses of said sequence or parts or derivatives thereof, as well as methods of using sequences from this gene or flanking sequences, or microsatellite markers in close vicinity to this gene in methods for selecting for one of the two alleles of this gene. Specifically provided are breeding methods using discrimination between dwarf fenotypes and non dwarf fenotypes, which are a result of the allele variation within this gene.

5 Claims, 14 Drawing Sheets

FIG. 1A

HMGIC cDNA

```
         10         20         30         40         50         60
CCGTGTGCTT CCCCCCGTCG CGAGGTGCCG CGCAGAGCCG GGCGGAGGGC TGAGCTCTCG 70         80         90        100        110        120
GCTCGCCATG AGCGCCCAAG GCGAGGGACC CGGCCAGTCT TCCACCGCCG CCCCGGAGCA 130        140        150        160        170        180
ACCTGCCGCC GCCGAGCCGC AGAAGCGAGG ACGAGGCAGA CCCAGGAAGC AGCCCCAAGA 190        200        210        220        230        240
ACCAACTGGT GAACCATCTC CTAAAAGACC AAGAGGAAGA CCCAAGGGAA GCAAAAACAA 250        260        270        280        290        300
GAGTCCCTCT AAAGCAGCTC AGAAGAAAGC AGAAGCCACT GGTGAAAAGC GACCCCGNGG 310        320        330        340        350        360
GCGGCCCAGA AAATGGCCTC AACAAGTGGT TCAAAAGAAG CCTGCTCAGG AAGAGACTGA 370        380        390        400        410
AGAAACATCG TCACAAGAAT CTGCAGAGGA AGACTAGGGG ACCGAACCAT
```

FIG. 1B

HMGIC cDNA                                                        LIMITS: 68  3

| | | | | | | | | 97 |
|---|---|---|---|---|---|---|---|---|
| ATG | AGC | GCC | CAA | GGC | GAG | GGA | CCC | CAG |
| Met | Ser | Ala | Gln | Gly | Glu | Gly | Pro | Gln |

| | | | | | | | | 127 |
|---|---|---|---|---|---|---|---|---|
| TCT | TCC | ACC | GCC | GCC | CCG | GAG | CAA | GCC |
| Ser | Ser | Thr | Ala | Ala | Pro | Glu | Gln | Ala |

| | | | | | | | | 157 |
|---|---|---|---|---|---|---|---|---|
| GCC | GCC | GAG | CCG | CAG | AAG | CGA | GGA | GGC |
| Ala | Ala | Glu | Pro | Gln | Lys | Arg | Gly | Gly |

| | | | | | | | | 187 |
|---|---|---|---|---|---|---|---|---|
| AGA | CCC | AGG | AAG | CAG | CCC | CAA | GAA | ACT |
| Arg | Pro | Arg | Lys | Gln | Pro | Gln | Glu | Thr |

| | | | | | | | | 217 |
|---|---|---|---|---|---|---|---|---|
| GGT | GAA | CCA | TCT | CCT | AAA | AGA | CCA | GGA |
| Gly | Glu | Pro | Ser | Pro | Lys | Arg | Pro | Gly |

FIG. 1C

| | | | | | | | | | 247<br>CCC<br>Pro |
|---|---|---|---|---|---|---|---|---|---|
| AGA<br>Arg | CCC<br>Pro | AAG<br>Lys | GGA<br>Gly | AGC<br>Ser | AAA<br>Lys | AAC<br>Asn | AAG<br>Lys | AGT<br>Ser | 277<br>GCC<br>Ala |
| TCT<br>Ser | AAA<br>Lys | GCA<br>Ala | GCT<br>Ala | CAG<br>Gln | AAG<br>Lys | AAA<br>Lys | GCA<br>Ala | GAA<br>Glu | 307<br>CCC<br>Pro |
| ACT<br>Thr | GGT<br>Gly | GAA<br>Glu | AAG<br>Lys | CGA<br>Arg | CCC<br>Pro | CGN | GGG<br>Gly | CGG<br>Arg | 337<br>AAG<br>Lys |
| AGA<br>Arg | AAA<br>Lys | TGG<br>Trp | CCT<br>Pro | CAA<br>Gln | CAA<br>Gln | GTG<br>Val | GTT<br>Val | CAA<br>Gln | 367<br>ACA<br>Thr |
| AAG<br>Lys | CCT<br>Pro | GCT<br>Ala | CAG<br>Gln | GAA<br>Glu | GAG<br>Glu | ACT<br>Thr | GAA<br>Glu | GAA<br>Glu | 397<br>TAG<br>End |
| TCG<br>Ser | TCA<br>Ser | CAA<br>Gln | GAA<br>Glu | TCT<br>Ser | GCA<br>Ala | GAG<br>Glu | GAA<br>Glu | GAC<br>Asp | |

FIG. 2A

| | |
|---|---|
| NAME: | LEI146 (LMU105) |
| PRIMER 1: | TCAAGCCACCAAAGTGCTTGG |
| PRIMER 2: | GATCACTCGCTCATAGCAGT |
| FRAGMENT LENGTH: | 258-276 bp |
| | |
| NAME: | LEI71 (LMU62) |
| PRIMER 1: | TCAGGTTAGTCTGACCATTGC |
| PRIMER 2: | TGAGTGTAAGATTGCTAATGGA |
| FRAGMENT LENGTH: | 281-330 bp |
| | |
| NAME: | UMA359 |
| PRIMER 1: | TTGATTTTGGTCAGTGCTT |
| PRIMER 2: | GGCAGCCAATCTGTCTTATT |
| FRAGMENT LENGTH: | 200-225 |
| | |
| NAME: | UMA364 (ISOLATED IN A DIFFERENT LAB, IS IDENTICAL TO (LEI146)) |
| PRIMER 1: | CCAGCATGTGATTCCCAAG |
| PRIMER 2: | AGTGTTTCCAGGGGCAAGGA |
| FRAGMENT LENGTH: | 160-170 |
| | |
| NAME: | ADL307 |
| PRIMER 1: | GCTGCTTAACTAAATGTTTG |
| PRIMER 2: | CAAGCGNCACTGACCCTGTC |
| FRAGMENT LENGTH: | 210-220 |
| | |
| NAME: | ADL234 |
| PRIMER 1: | CCCTGGGGCTCCCTCAGCAC |
| PRIMER 2: | CTGGACGCGTGAAAAAGTTC |
| FRAGMENT LENGTH: | 160-170 |
| | |
| NAME: | ADLI50 |
| PRIMER 1: | ATGCCAAGCATTACAGAAGC |
| PRIMER 2: | CCTGCAGCACCTTTATCTCT |
| FRAGMENT LENGTH: | 155-165 |
| | |
| NAME: | ADLI88 |
| PRIMER 1: | CACTTCCAGTATTAACGTGA |
| PRIMER 2: | GTGGACACAATGAGTTCCTC |
| FRAGMENT LENGTH: | 125-135 |
| | |
| NAME: | MCW43 (LGAL4) |
| PRIMER 1: | TGACTACTTTGATACGCATGGAGA |
| PRIMER 2: | CACCAAGTAGACGAAAACACATTT |
| FRAGMENT LENGTH: | 130-140 |

FIG. 2B

| | |
|---|---|
| NAME: | MCW44 (H5) |
| PRIMER 1: | AGTCCGAGCTCTGCTCGCCTCATA |
| PRIMER 2: | ACAGTGGCTCAGTGGGAAGTGACC |
| FRAGMENT LENGTH: | 140-147 |
| NAME: | MCW289 |
| PRIMER 1: | TAGTGCAGAAAGACAAGGCAG |
| PRIMER 2: | GATCCTTCCTCCTTCACTGG |
| FRAGMENT LENGTH: | 217-234 |
| NAME: | MCW297 |
| PRIMER 1: | TGCCAAACATGACCTCCAGTC |
| PRIMER 2: | ACTTCACTGCAGGGTGGTGAG |
| FRAGMENT LENGTH: | 288-303 |
| NAME: | MCWI9 |
| PRIMER 1: | CCCAGATTGATTTCATCATTCAAG |
| PRIMER 2: | GCATCTCCTCTCTACAGCCATGAA |
| FRAGMENT LENGTH: | 135-145 |
| NAME: | MCW 112 |
| PRIMER 1: | ATCTCTCTGCCCATGTTTCAG |
| PRIMER 2: | GATCACTAAGGTCCCTTTCAA |
| FRAGMENT LENGTH: | 270-280 |
| NAME: | MCWI8 |
| PRIMER 1: | GGAATTTGAACACCTGAGATTTCC |
| PRIMER 2: | CACTATGTTTATGGCAAACTCCTG |
| FRAGMENT LENGTH: | 210-230 |

FIG. 5A

HMGIc GENOMIC

```
         10         20         30         40         50         60
CCCAGTTTAC CGTCTGTGTC CTGAAAGGCC CAGCACGTTG GTTAAATGAG CAGCATAAGA
         70         80         90        100        110        120
GTGTTGCGTT CANNCAGGTG TGCTGAAAGG AGAGACAAAG TTGGCTTTGG NACGGAGGAG
        130        140        150        160        170        180
GATGGCCANN AAGGGANCGA AAGCTTCCCA CAGCACCCCC TTCACGTTGG ATATCTGCTC
        190        200        210        220        230        240
GAAANTGCTT CTCATAGGAG ATCCATGACA GAGCATGGCA GGGATTTCTC TTTCTTGGTA
        250        260        270        280        290        300
GCCTGTGGGG TAGGAGGGAA GAGCAGCTAA CTAAAGTGGT GTGGTCTGAG AGTGGAGAGC
        310        320        330        340        350        360
TTCCCCTGCT CTCTACAGTG TCTTCCTGAG GCATCACAGC AGCTGTACAG CACATTTGT
        370        380        390        400        410        420
GAGCTTGGGA TGCAGTTGTC AGCTGTGCGA GAGGAGGCAG CCTTGGATGC ATGGTCACCA
```

FIG. 5B

```
         430       440       450       460       470       480
    CATACTTATT TTTTTCTTT TTGTTTATTC TAGGAAGAGA CTGAAGAAAC ATCGTCACAA
         490       500       510       520       530       540
    GAATCTGCAG AGGAAGACTA GGAGACCGCA CCATGCAATT TCTACCTCAT CAGCAGTTGG

HMGIc GENOMIC
         550       560       570       580       590       600
    GTCTTTTGAA GGGAGAAGAC ACTGCCTTGA CCACTTATTT TCTANTGCCA TGGTCTTTCC
         610       620       630       640       650
    ACTTTTGCCT GGGGGGAAAA AAATTGCATA ACCTTAAAAR GGTTTTGCCT A
```

FIG. 7 DISTRIBUTION BODY WEIGHTS AFTER CORRECTION FOR SEX, PERIOD AND FAMILY EFFECTS.

FIG. 8 COMPARISON OF LMU 105 GENOTYPES AND BODY WEIGHTS FROM NON-DWARF ANIMALS.

SEQUENCE LISTING

<160> NUMBER OF SEQ ID NOS: 34

<210> SEQ ID NO 1
<211> LENGTH: 410
<212> TYPE: DNA
<213> ORGANISM: Chicken
<220> FEATURE:
<221> NAME/KEY: unsure
<222> LOCATION: (298)..(298)
<223> OTHER INFORMATION: n is unknown

<400> SEQUENCE: 1

```
ccgtgtgctt cccccgtcg cgaggtgccg cgcagagccg ggcggagggc tgagctctcg      60
gctcgccatg agcgcccaag gcgagggacc cggccagtct tccaccgccg ccccggagca    120
acctgccgcc gccgagccgc agaagcgagg acgaggcaga cccaggaagc agccccaaga    180
accaactggt gaaccatctc ctaaaagacc aagaggaaga cccaagggaa gcaaaaacaa    240
gagtccctct aaagcagctc agaagaaagc agaagccact ggtgaaaagc gaccccgngg    300
gcggcccaga aaatggccct aacaagtggt tcaaaagaag cctgctcagg aagagactga    360
```

```
agaaacatcg tcacaagaat ctgcagagga agactagggg accgaaccat         410
```

<210> SEQ ID NO 2
<211> LENGTH: 109
<212> TYPE: PRT
<213> ORGANISM: Chicken
<220> FEATURE:
<221> NAME/KEY: unsure
<222> LOCATION: (77)..(77)
<223> OTHER INFORMATION: X is unknown

<400> SEQUENCE: 2

```
Met Ser Ala Gln Gly Glu Gly Pro Gly Gln Ser Ser Thr Ala Ala Pro
1               5                   10                  15
Glu Gln Pro Ala Ala Glu Pro Gln Lys Arg Gly Arg Gly Arg Pro
            20                  25                  30
Arg Lys Gln Pro Gln Glu Pro Thr Gly Glu Pro Ser Pro Lys Arg Pro
        35                  40                  45
Arg Gly Arg Pro Lys Gly Ser Lys Asn Lys Ser Pro Ser Lys Ala Ala
    50                  55                  60
Gln Lys Lys Ala Glu Ala Thr Gly Glu Lys Arg Pro Xaa Gly Arg Pro
65                  70                  75                  80
Arg Lys Trp Pro Gln Gln Val Val Gln Lys Lys Pro Ala Gln Glu Glu
                85                  90                  95
Thr Glu Glu Thr Ser Ser Gln Glu Ser Ala Glu Glu Asp
            100                 105
```

<210> SEQ ID NO 3
<211> LENGTH: 330
<212> TYPE: DNA
<213> ORGANISM: Chicken
<220> FEATURE:
<221> NAME/KEY: unsure
<222> LOCATION: (231)..(231)
<223> OTHER INFORMATION: n is unknown

<400> SEQUENCE: 3

```
atgagcgccc aaggcgaggg acccggccag tcttccaccg ccgccccgga gcaacctgcc    60
gccgccgagc cgcagaagcg aggacgaggc agacccagga agcagcccca agaaccaact   120
ggtgaaccat ctcctaaaag accaagagga agacccaagg gaagcaaaaa caagagtccc   180
tctaaagcag ctcagaagaa agcagaagcc actggtgaaa agcgacccg nggcggccc    240
agaaaatggc ctcaacaagt ggttcaaaag aagcctgctc aggaagagac tgaagaaaca   300
tcgtcacaag aatctgcaga ggaagactag                                    330
```

<210> SEQ ID NO 4
<211> LENGTH: 21
<212> TYPE: DNA
<213> ORGANISM: Unknown
<220> FEATURE:
<223> OTHER INFORMATION: OTHER INFORMATION:Oligonucleotide primer

<400> SEQUENCE: 4

```
tcaagccacc aaagtgcttg g                                              21
```

<210> SEQ ID NO 5
<211> LENGTH: 20
<212> TYPE: DNA
<213> ORGANISM: Unknown
<220> FEATURE:
<223> OTHER INFORMATION: OTHER INFORMATION:Oligonucleotide primer -continued

```
<400> SEQUENCE: 5
gatcactcgc tcatagcagt                                           20

<210> SEQ ID NO 6
<211> LENGTH: 21
<212> TYPE: DNA
<213> ORGANISM: Unknown
<220> FEATURE:
<223> OTHER INFORMATION: OTHER INFORMATION:Oligonucleotide primer

<400> SEQUENCE: 6
tcaggttagt ctgaccattg c                                         21

<210> SEQ ID NO 7
<211> LENGTH: 22
<212> TYPE: DNA
<213> ORGANISM: Unknown
<220> FEATURE:
<223> OTHER INFORMATION: OTHER INFORMATION:Oligonucleotide primer

<400> SEQUENCE: 7
tgagtgtaag attgctaatg ga                                        22

<210> SEQ ID NO 8
<211> LENGTH: 19
<212> TYPE: DNA
<213> ORGANISM: Unknown
<220> FEATURE:
<223> OTHER INFORMATION: OTHER INFORMATION:Oligonucleotide primer

<400> SEQUENCE: 8
ttgattttgg tcagtgctt                                            19

<210> SEQ ID NO 9
<211> LENGTH: 20
<212> TYPE: DNA
<213> ORGANISM: Unknown
<220> FEATURE:
<223> OTHER INFORMATION: OTHER INFORMATION:Oligonucleotide primer

<400> SEQUENCE: 9
ggcagccaat ctgtcttatt                                           20

<210> SEQ ID NO 10
<211> LENGTH: 19
<212> TYPE: DNA
<213> ORGANISM: Unknown
<220> FEATURE:
<223> OTHER INFORMATION: OTHER INFORMATION:Oligonucleotide primer

<400> SEQUENCE: 10
ccagcatgtg attcccaag                                            19

<210> SEQ ID NO 11
<211> LENGTH: 20
<212> TYPE: DNA
<213> ORGANISM: Unknown
<220> FEATURE:
<223> OTHER INFORMATION: OTHER INFORMATION:Oligonucleotide primer

<400> SEQUENCE: 11
agtgtttcca ggggcaagga                                           20

<210> SEQ ID NO 12
<211> LENGTH: 20
```

```
<212> TYPE: DNA
<213> ORGANISM: Unknown
<220> FEATURE:
<223> OTHER INFORMATION: OTHER INFORMATION:Oligonucleotide primer

<400> SEQUENCE: 12
gctgcttaac taaatgtttg                                                    20

<210> SEQ ID NO 13
<211> LENGTH: 20
<212> TYPE: DNA
<213> ORGANISM: Unknown
<220> FEATURE:
<223> OTHER INFORMATION: OTHER INFORMATION:Oligonucleotide primer
<221> NAME/KEY: unsure
<222> LOCATION: (7)..(7)
<223> OTHER INFORMATION: n is unknown

<400> SEQUENCE: 13
caagcgncac tgaccctgtc                                                    20

<210> SEQ ID NO 14
<211> LENGTH: 20
<212> TYPE: DNA
<213> ORGANISM: Unknown
<220> FEATURE:
<223> OTHER INFORMATION: OTHER INFORMATION:Oligonucleotide primer

<400> SEQUENCE: 14
ccctggggct ccctcagcac                                                    20

<210> SEQ ID NO 15
<211> LENGTH: 20
<212> TYPE: DNA
<213> ORGANISM: Unknown
<220> FEATURE:
<223> OTHER INFORMATION: OTHER INFORMATION:Oligonucleotide primer

<400> SEQUENCE: 15
ctggacgcgt gaaaaagttc                                                    20

<210> SEQ ID NO 16
<211> LENGTH: 20
<212> TYPE: DNA
<213> ORGANISM: Unknown
<220> FEATURE:
<223> OTHER INFORMATION: OTHER INFORMATION:Oligonucleotide primer

<400> SEQUENCE: 16
atgccaagca ttacagaagc                                                    20

<210> SEQ ID NO 17
<211> LENGTH: 20
<212> TYPE: DNA
<213> ORGANISM: Unknown
<220> FEATURE:
<223> OTHER INFORMATION: OTHER INFORMATION:Oligonucleotide primer

<400> SEQUENCE: 17
cctgcagcac ctttatctct                                                    20

<210> SEQ ID NO 18
<211> LENGTH: 20
<212> TYPE: DNA
<213> ORGANISM: Unknown
<220> FEATURE:
<223> OTHER INFORMATION: OTHER INFORMATION:Oligonucleotide primer
```

```
<400> SEQUENCE: 18
cacttccagt attaacgtga                                              20

<210> SEQ ID NO 19
<211> LENGTH: 20
<212> TYPE: DNA
<213> ORGANISM: Unknown
<220> FEATURE:
<223> OTHER INFORMATION: OTHER INFORMATION:Oligonucleotide primer

<400> SEQUENCE: 19
gtggacacaa tgagttcctc                                              20

<210> SEQ ID NO 20
<211> LENGTH: 24
<212> TYPE: DNA
<213> ORGANISM: Unknown
<220> FEATURE:
<223> OTHER INFORMATION: OTHER INFORMATION:Oligonucleotide primer

<400> SEQUENCE: 20
tgactacttt gatacgcatg gaga                                         24

<210> SEQ ID NO 21
<211> LENGTH: 24
<212> TYPE: DNA
<213> ORGANISM: Unknown
<220> FEATURE:
<223> OTHER INFORMATION: OTHER INFORMATION:Oligonucleotide primer

<400> SEQUENCE: 21
caccaagtag acgaaaacac attt                                         24

<210> SEQ ID NO 22
<211> LENGTH: 24
<212> TYPE: DNA
<213> ORGANISM: Unknown
<220> FEATURE:
<223> OTHER INFORMATION: OTHER INFORMATION:Oligonucleotide primer

<400> SEQUENCE: 22
agtccgagct ctgctcgcct cata                                         24

<210> SEQ ID NO 23
<211> LENGTH: 24
<212> TYPE: DNA
<213> ORGANISM: Unknown
<220> FEATURE:
<223> OTHER INFORMATION: OTHER INFORMATION:Oligonucleotide primer

<400> SEQUENCE: 23
acagtggctc agtgggaagt gacc                                         24

<210> SEQ ID NO 24
<211> LENGTH: 21
<212> TYPE: DNA
<213> ORGANISM: Unknown
<220> FEATURE:
<223> OTHER INFORMATION: OTHER INFORMATION:Oligonucleotide primer

<400> SEQUENCE: 24
tagtgcagaa agacaaggca g                                            21

<210> SEQ ID NO 25
```

```
<211> LENGTH: 20
<212> TYPE: DNA
<213> ORGANISM: Unknown
<220> FEATURE:
<223> OTHER INFORMATION: OTHER INFORMATION:Oligonucleotide primer

<400> SEQUENCE: 25
gatccttcct ccttcactgg                                               20

<210> SEQ ID NO 26
<211> LENGTH: 21
<212> TYPE: DNA
<213> ORGANISM: Unknown
<220> FEATURE:
<223> OTHER INFORMATION: OTHER INFORMATION:Oligonucleotide primer

<400> SEQUENCE: 26
tgccaaacat gacctccagt c                                             21

<210> SEQ ID NO 27
<211> LENGTH: 21
<212> TYPE: DNA
<213> ORGANISM: Unknown
<220> FEATURE:
<223> OTHER INFORMATION: OTHER INFORMATION:Oligonucleotide primer

<400> SEQUENCE: 27
acttcactgc agggtggtga g                                             21

<210> SEQ ID NO 28
<211> LENGTH: 24
<212> TYPE: DNA
<213> ORGANISM: Unknown
<220> FEATURE:
<223> OTHER INFORMATION: OTHER INFORMATION:Oligonucleotide primer

<400> SEQUENCE: 28
cccagattga tttcatcatt caag                                          24

<210> SEQ ID NO 29
<211> LENGTH: 24
<212> TYPE: DNA
<213> ORGANISM: Unknown
<220> FEATURE:
<223> OTHER INFORMATION: OTHER INFORMATION:Oligonucleotide primer

<400> SEQUENCE: 29
gcatctcctc tctacagcca tgaa                                          24

<210> SEQ ID NO 30
<211> LENGTH: 21
<212> TYPE: DNA
<213> ORGANISM: Unknown
<220> FEATURE:
<223> OTHER INFORMATION: OTHER INFORMATION:Oligonucleotide primer

<400> SEQUENCE: 30
atctctctgc ccatgtttca g                                             21

<210> SEQ ID NO 31
<211> LENGTH: 21
<212> TYPE: DNA
<213> ORGANISM: Unknown
<220> FEATURE:
<223> OTHER INFORMATION: OTHER INFORMATION:Oligonucleotide primer

<400> SEQUENCE: 31
```

```
gatcactaag gtccctttca a                                                    21

<210> SEQ ID NO 32
<211> LENGTH: 24
<212> TYPE: DNA
<213> ORGANISM: Unknown
<220> FEATURE:
<223> OTHER INFORMATION: OTHER INFORMATION:Oligonucleotide primer

<400> SEQUENCE: 32
ggaatttgaa cacctgagat ttcc                                                 24

<210> SEQ ID NO 33
<211> LENGTH: 24
<212> TYPE: DNA
<213> ORGANISM: Unknown
<220> FEATURE:
<223> OTHER INFORMATION: OTHER INFORMATION:Oligonucleotide primer

<400> SEQUENCE: 33
cactatgttt atggcaaact cctg                                                 24

<210> SEQ ID NO 34
<211> LENGTH: 651
<212> TYPE: DNA
<213> ORGANISM: Chicken
<220> FEATURE:
<221> NAME/KEY: unsure
<222> LOCATION: (73)..(74)
<223> OTHER INFORMATION: n is unknown
<221> NAME/KEY: unsure
<222> LOCATION: (111)..(111)
<223> OTHER INFORMATION: n is unknown
<221> NAME/KEY: unsure
<222> LOCATION: (129)..(130)
<223> OTHER INFORMATION: n is unknown
<221> NAME/KEY: unsure
<222> LOCATION: (137)..(137)
<223> OTHER INFORMATION: n is unknown
<221> NAME/KEY: unsure
<222> LOCATION: (185)..(185)
<223> OTHER INFORMATION: n is unknown
<221> NAME/KEY: unsure
<222> LOCATION: (585)..(585
<223> OTHER INFORMATION: n is unknown

<400> SEQUENCE: 34
cccagtttac cgtctgtgtc ctgaaaggcc cagcacgttg gttaaatgag cagcataaga          60
gtgttgcgtt canncaggtg tgctgaaagg agagacaaag ttggctttgg nacggaggag         120
gatggccann aagggancga aagcttccca cagcaccccc ttcacgttgg atatctgctc         180
gaaantgctt ctcataggag atccatgaca gagcatggca gggatttctc tttcttggta         240
gcctgtgggg taggagggaa gagcagctaa ctaaagtggt gtggtctgag agtgagagc          300 ttcccctgct ctctacagtg tcttcctgag gcatcacagc agctgtacag cacattttgt         360
gagcttggga tgcagttgtc agctgtgcga gaggaggcag ccttggatgc atggtcacca         420
catacttatt ttttttcttt ttgtttattc taggaagaga ctgaagaaac atcgtcacaa         480
gaatctgcag aggaagacta ggagaccgca ccatgcaatt tctacctcat cagcagttgg         540
gtcttttgaa gggagaagac actgccttga ccacttattt tctantgcca tggtctttcc         600
acttttgcct gggggaaaa aaattgcata accttaaaar ggttttgcct a                   651
```

SELECTION FOR DWARFISM IN POULTRY

BACKGROUND OF THE INVENTION

The present invention relates to the field of agriculture, in particular to animal breeding, more specifically to the breeding of poultry. In breeding poultry selection of animals to breed with is a very important aspect. Traditional selection methods have been applied for centuries. It is therefore quite difficult to improve breeding stocks of poultry in important phenotypic characteristics using traditional selection methods.

Modern biotechnology has provided a number of novel tools for localizing traits on the genetic level, together with means of detecting the different alleles of such traits and thus providing the ability to select animals having the right allele. One of the novel ways of identifying a gene related to a useful trait involves so-called microsatellite markers.

Microsatellites are direct repeats of di, tri or tetra nucleotides such as $(TG)_n$, $(TA)_n$, $(CAC)_n$ or $(GGAT)_n$ where n can vary from 4 to over 30. (Crooijmans et al, 1993). There repeating DNA elements are found almost randomly throughout the vertebrate genome. Their number, over $10^4$ in a vertebrate genome, and their extreme polymorphism makes them useful for linkage analysis. It is possible to detect different alleles, resulting from variation in the number of repeats, by PCR using locus specific oligonucleotides. From 1993, different laboratories have been working on the construction of a chicken genetic map using these microsatellite markers.

This genetic map facilitates linking of Quantitative Trait Loci (QTLs), single gene traits and non-single gene traits, with microsatellite data in order to identify their chromosomal location(s) (Crooijmans et al., 1993; 1994; 1995; 1996a; Cheng and Crittenden, 1994; Burt et al., 1995).

Today, the chicken genetic map covers about 90% of the genome. In order to be useful for linkage studies, a genetic map should have a marker at every 20 centi Morgans ("cM") of the linkage map, which is still approximately $1.10^7$ basepair. Then a QTL will always be within ten percent recombination from a microsatellite marker, the maximum crossover percentage where usage of markers is still useful (Van der Beek and Van Arendonk, 1993).

In a recent study, Ruyter-Spira et al. (Poultry Science, in press) mapped the Dominant White locus in chicken using microsatellite markers. This gene was successfully mapped on linkage group 22 of the East Lansing International reference family near MCW188. This study proves that it is now possible to successfully map monogenic traits (i.e. the Dominant White trait) by means of a so-called total genome scan. For this purpose, microsatellite markers of high quality (many alleles, almost evenly spread performance of the PCR product) covering the major part of the chicken genome can be used.

Bulked Segregant Analysis in Combination with Microsatellite Markers

In a linkage study, a large number of animals from segregating populations have to be genotyped. When a cross is set up to study a single locus trait with a dominant or a recessive phenotype, it is possible to sample the DNA of the animals with the same phenotype. These two pools will only differ for the region that is closely linked to the phenotype on which the pools were selected, and they will be similar to all other non-linked regions. Therefore, the distribution of the different alleles of an informative marker will only show a difference between these two pools if the marker is closely linked to the gene causing the different phenotype. Identification of the chromosomal region of interest is possible when a microsatellite map covering the whole genome is available, because linkage between the gene of interest and the microsatellite marker(s) can be detected. Using this so-called bulked segregant analysis, it is possible to carry out a 'total genome scan' on pooled samples, which greatly reduces the amount of genotypings that have to be carried out. Today, over 600 chicken microsatellite markers are available, covering over 90% of the chicken genome. This makes it possible to make a selection of approximately 150 well-working markers that efficiently can be used for a total genome scan. In a recent experiment, Ruyter-Spira et al. (Poultry Science, in press) successfully mapped the Dominant White locus using pooled samples. A limited number of possibly linked microsatellite markers (4 out of 68 informative markers) was tested on individual samples, finally resulting in the identification of the chromosomal region of the gene. Thus pooling of DNA proved to greatly reduce the amount of PCRs and analyses to perform.

In the study of Ruyter-Spira et al., a dominant trait was successfully mapped on the chicken chromosome. However, many traits are not regulated by single genes. When segregating populations for complex traits are available, it would be theoretically possible to identify the chromosomal regions of interest using a bulked segregant approach. Puel et al. (1995) used mouse microsatellite markers to identify chromosomal regions endowed with antibody production in Biozzi mice, mice selected for High and Low antibody responses to Sheep Red Blood Cells. They carried out a total genome scan using 90 polymorphic microsatellite markers on 60 individual $F_2$ animals, selected for their extreme phenotype from a total $F_2$ population of 240 animals.

However, though it may be possible to localize dominant traits which can be attributed to a single gene to a region of a chromosome, or even regions where different parts of complex traits may be found, it is by no means clear that every complex trait can be localized using this approach, nor that for instance recessive traits can be localized using microsatellite markers. Moreover, even though a trait has been localized to the extent that it has been found associated with some microsatellite markers, this in no way means that a responsible gene for the trait has been identified. Usually the distance between two microsatellite markers is still in the order of about 400–600 Kb, which is much larger than any usual gene sequence. Furthermore, when contemplating how to localize the regions on one or more chromosomes associated with a certain phenotype, one does not know whether this will be a single gene trait or a complex one.

The present invention in one embodiment provides the localization of a trait on a chicken chromosome, as well as a gene associated with said trait.

The trait to which the present invention relates is so called autosomal dwarfism. Hereunder a short introduction into dwarfism in chicken is presented for explanatory purposes.

Crawford (1990) lists three sex-linked forms and one autosomal form of dwarfism in chicken: dominant sex-linked dwarfism (Z), recessive sex-linked dwarfism (rg), sex-linked dwarfism (dw) and autosomal dwarfism (adw). Of the first three, the sex-linked dwarfing allele (dw) is the most studied one. This recessive sex-linked dwarfism is caused by a dysfunctional Growth Hormone receptor (GHR) which causes absence of Growth Hormone (GH)-dependent gene expression in the chicken liver. This defect seems to be the chicken equivalent of Laron dwarfism in humans: despite high circulating GH concentrations, plasma Insulin-like Growth Factor-I (IGF-I) levels are extremely low (Huybrechts et al., 1985; Bowen et al., 1987; Duriez et al., 1993). A point mutation located within the part of the gene encoding the extracellular domain of the GH receptor is responsible for the dysfunctional receptor (Duriez et al., 1993). The sexlinked dwarfism chicken is now being used as an animal model for Laron Dwarfism in humans and these animals are also used to study genes regulated by Growth Hormone (Agarwal et al., 1995; Tanaka et al., 1996). Recent research revealed that IGF-I mRNA is expressed in the liver in a GH-dependent manner after hatching. In extrahepatic tissues, mRNA expression is independent of GH and GHR before and after hatching, except for the testis, where GH seems to inhibit IGF-I mRNA expression. In dwarf chickens, hepatic IGF-I expression is completely abolished (Tanaka et al., 1996).

In the Cornell K strain White Leghorn chicken, an autosomal recessive gene (adw) exists causing a 30% reduced size and body weight, later sexual maturity, lower hatching rate and production of less eggs (reduction of 10%). The adult body weight is about 1400 g. However, these dwarfs have excellent viability (Crawford, 1990). This autosomal dwarfism in fowl was already reported many years ago (Cole, 1973) but the nature of the gene causing this type of dwarfism is not known yet. Dwarf animals can be recognised at birth but their phenotype is more apparent at six weeks of age. These animals also have shorter legs (Scanes et al., 1983; Bowen et al., 1987) and a striking large skull compared to the rest of the body (Euribrid BV, personal communication). Phenotypically, heterozygous animals cannot be separated from homozygous animals: chicken which have the dwarf phenotype have the adw/adw genotype and the chicken which have non-dwarf phenotype carry at least one copy of the dominant allele (Adwl/*). Leenstra and Pit (1984) therefore suggested the use of the gene in commercial stocks in order to reduce body size and feed requirements. It is nor known whether this particular gene is present in any of the bantam breeds (Crawford, 1990).

In a few studies, comparisons have been made between the sex-linked dwarfism (dw) and the autosomal dwarfism (adw) in chicken. However, information on the autosomal dwarfism is limited. The first comparative study on autosomal recessive dwarfism and sexlinked dwarfism was carried out by Scanes et al. in 1983, ten years before the discovery of the genetic defect by Duriez et al. in 1993. They concluded that neither autosomal dwarfism nor sex-linked dwarfism appeared to be caused by hypopituitarism. Huybrechts et al. (1985) studied plasma concentrations of somatomedin-C (IGF-1) in sex-linked dwarf and autosomal dwarf chicken. Plasma concentrations of IGF-I in sex-linked dwarf chicken were reduced, but were unaffected in autosomal dwarf chicken. GH levels in autosomal dwarf animals were normal. Scanes et al. (1983) found that plasma concentrations of triiodothyronine ($T_3$) were depressed in sex-linked dwarf chicken, where those of thyroxine ($T_4$) were normal and those of GE were raised. We now know that this must be caused by physiological changes caused by the dysfunctional growth hormone receptor. Lauterio et al (1986) indeed suggested a dependency of $T_3$ levels on GH levels. In autosomal dwarf animals, only a slight decrease in $T_3$ and $T_4$ was observed. The minuteness of these changes suggested that this is not the cause of the dwarf phenotype in these animals. The absence of major differences between the plasma concentrations of $T_3$ and $T_4$ in the autosomal dwarf chicks is thus consistent with the observed situation for GH and IGF-I. It would therefore appear that the lesion in the autosomal dwarfs may not be of an endocrine nature (Huybrechts et al., 1985).

In other vertebrate animals, such as mice and man, a number of forms of dwarfism have been identified as well. Many of these forms are also related to the Growth-Hormone-Insulin-like Growth Factor pathway. However, in mice a form of dwarfism not related to this pathway has been found as well. A mouse having such a form of dwarfism is the pygmy mouse, which is an autosomal recessive trait. This form has been attributed to a mutation in a gene called HMGI-C. This gene is also present in the human genome (located on chromosome 12) but has not been associated with a dwarf syndrome in humans. In chickens or in other birds, such as turkey, duck or goose, a homologue of the HMGI-C gene has not been found, and, considering the appreciable heterology that exists between mammalian and avian genomic nucleotide sequences, it is generally expected that screening a random library of avian genomic sequences with probes obtained from distantly related mammalian genomic sequences is not the most promising approach.

BRIEF DESCRIPTION OF THE DRAWINGS

FIG. 1A provides the nucleotide sequence of HMGIC cDNA (SEQ ID NO:1).

FIGS. 1B–1C illustrate the HMGIC cDNA open reading frame.

FIG. 2A provides nucleotide sequences of nine pairs of PCR primers employed in the methods of the invention that are identified as: LEI146 (LMU105) (SEQ ID NOs:4–5); LEI71 (LMU62) (SEQ ID NOs:6–7); UMA359 (SEQ ID NOs:8–9); UMA364 (SEQ ID NOs:10–11); ADL307 (SEQ ID NOs:12–13); ADL234 (SEQ ID NOs:14–15); ADL150 (SEQ ID NOs:16–17); ADL188 (SEQ ID NOs:18–19); and MCW43(LGAL4) (SEQ ID NOs:20–21).

FIG. 2B provides nucleotide sequences of six pairs of PCR primers employed in the methods of the invention that are identified as MCW44 (H5) (SEQ ID NO:22–23); MCW289 (SEQ ID NOs:24–25); MCW297 (SEQ ID NOs:26–27); MCW19 (SEQ ID NOs:28–29); MCW112 (SEQ ID NOs:30–31); and MCW18 (SEQ ID NOs:32–33).

FIGS. 5A–5B illustrate the nucleic acid sequence of the HMGI-c genomic DNA.

SUMMARY OF INVENTION

Figure 3:
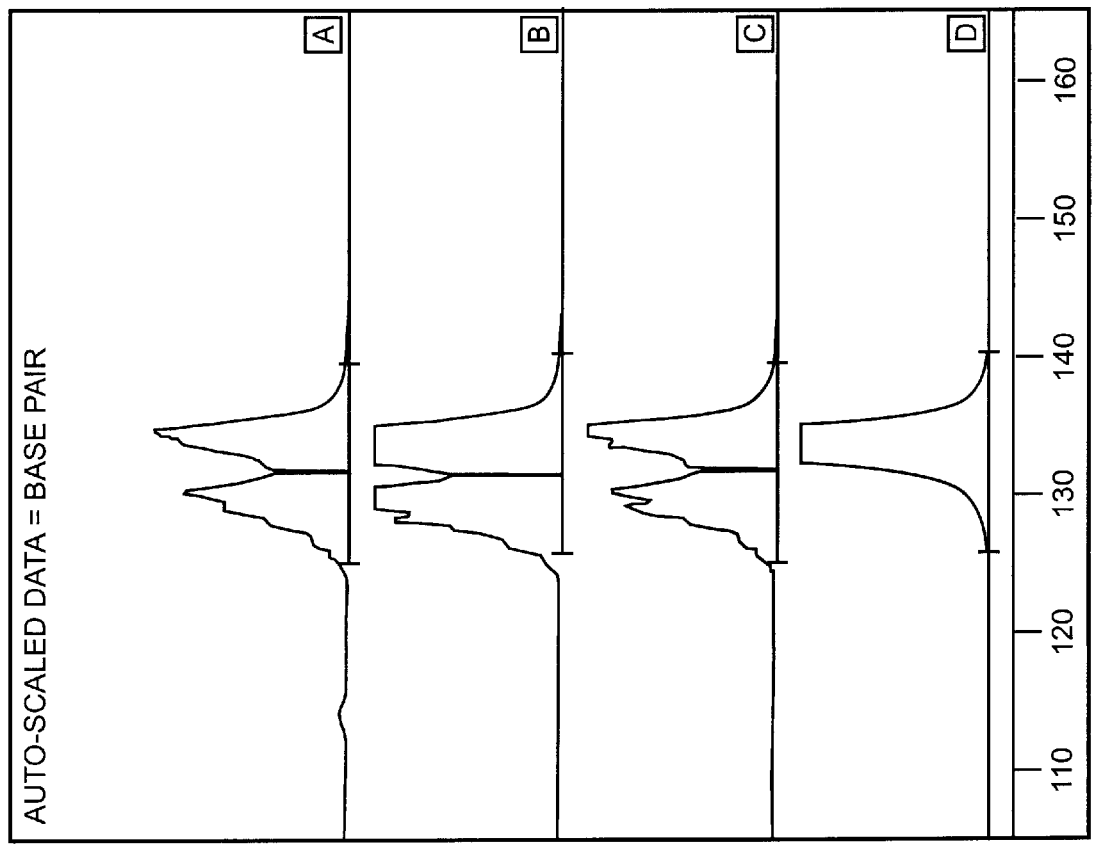
FIG. 3 illustrates the differences in allelic distribution on MCW' in family 25/880. Both parents (boxes A and B) carry the 130 bp and 134 bp alleles. The non-dwarf animals, box C, also carry both alleles, but the dwarf animals, box D, only carry the 134 bp allele.

The present invention provides the localization of a gene responsible for autosomal dwarfism in poultry. This gene is localized within 6 Megabases, more likely 2 Megabases of the microsatellite marker LEI146. It very likely lies within 2 centi Morgan of said marker LEI146. The gene can also be defined as having a Lod-score with LEI146 of at least 10, but preferably at least 20, more preferably at least 25 as can be discerned from FIG. 9 (A reference for the location of the LEI146 marks is R. P. M. A. Crooymans at al. in Animal Genetics 1997, Vol. 28).

DETAILED DESCRIPTION OF THE PREFERRED EMBODIMENTS

The present invention, in a preferred embodiment, provides a solution for the fact that on the one hand, even when a trait has been associated with some microsatellite markers, this in no way means that a responsible gene for the trait has been identified, whereas on the other hand screening a random library of avian genomic sequences with probes obtained from distantly related mammalian genomic sequences will not lead to the proper identification of the wanted gene. The invention provides a combination of the bulked segregant analysis, where a trait is linked to microsatellite markers with the screening of a thus selected genomic library with probes derived from the supposedly heterologous gene. An important aspect of the present invention is that the combination of first mapping the gene for autosomal dwarfism to a certain location on chromosome 1 using microsatellite-markers, thereby enabling identification of the homologous chromosome segment in man and mice, through the presence of earlier mapped genes on said location at chromosome 1 (in particular Ly2 and especially Igf-1), provided two candidate genes for autosomal dwarfism, of which HMGI-C was identified as a very likely candidate by means of cleverly selected probes. Specifically, the invention provides the localisation of the Adw/adw gene between two microsatellite markers, MCW43(LGAL4 gene) and MCW18, close to markers UMA364 and LEI146, and in addition shows that a chicken gene hybridising with the murine HMGI-C can be found at the same location. Thus the Adw/adw dwarfism trait is associated with the HMGI-C gene.

The thus identified gene was cloned and cDNA was obtained with the sequence as shown in FIG. 1.

The invention thus provides a recombinant nucleic acid having a sequence comprising at least a functional part of a gene responsible for autosomal dwarfism, particularly the HMGI-C gene or a functional derivative thereof of an avian species. Since avian genomes will be more homologous among each other than when compared with a mammalian genome, the invention also provides the recombinant nucleic acid having a sequence comprising at least a functional part of a gene responsible for autosomal dwarfism, particularly the HMGI-C gene or a functional derivative thereof of such avian species as chickens, turkeys, ducks or geese. In particular, the invention provides the alleles of genes which relate to autosomal dwarfism found in birds, which in the recessive homozygous form lead to the phenotype dwarf. The average skilled expert will now be able to design or construct a nucleic acid probe capable of distinguishing the 'dwarf' allele of the gene responsible for autosomal dwarfism, particularly HMGI-C gene from the non-dwarf allele and method for detecting alleles of a gene responsible for autosomal dwarfism, particularly the HMGI-C gene comprising hybridization of at least one nucleic acid probe to a sample comprising at least a functional part of such a gene, possibly involving amplification involving said gene. Amplification methods are widely known in the art. With such probes and methods a testkit for distinguishing between alleles of a gene responsible for autosomal dwarfism, particularly the HMGI-C gene, for instance comprising at least one nucleic acid probe and a hybridization buffer, and possibly in addition a nucleic acid polymerase, can be developed. Using such a method or testkit can be applied for selecting birds, such us chicken, turkeys, ducks or geese which are homozygous for the 'dwarf'-allele of the gene responsible for autosomal dwarfism, particularly the HMGI-C gene, can be selected which is method for making a breeding line consisting of 'dwarf'-birds, comprising selecting birds homozygous for the dwarf' allele of the gene responsible for autosomal dwarfism, particularly the HMGI-C gene.

Such birds can be employed in methods for breeding birds comprising crossing a bird from a breeding line with non-dwarf birds. In particular, broiler birds (which are used for meat production) such as broiler chickens can then be inexpensively produced by employing one parent line that is homozygous for the dwarf allele and another that is homozygous for the non-dwarf allele. The resulting heterozygous progeny will all be not dwarf.

DETAILED DESCRIPTION OF THE INVENTION

Experimental Part

Animals for Microsatellite Analysis

A segregating population for the autosomal dwarf Locus was obtained by crossing White Leghorn cocks, homozygous recessive on the putative autosomal dwarfism locus (adw/adw) with Cornish hens not carrying the recessive allele (Adw/Adw). The $F_1$ (Adw/adw,) cocks (26) and hens (50) were crossed and a $F_2$ generation was bred in five progeny batches per parental cross. After birth, animals were phenotyped: 'sure dwarf, 'probably dwarf' and 'non-dwarf'. Blood samples from the first four batches $F_2$ chickens were collected at approximately six weeks of age and animals were weighed and phenotyped again at this time point. Now animals were separated in three groups: 'sure dwarf', 'probably dwarf/probably non-dwarf' and 'sure non-dwarf'. Because phenotyping at six weeks of age is far more reliable than phenotyping at birth, these groups were used for analysis. Of these groups, the 'sure dwarf' and 'sure non-dwarf' animals of five crosses were used for the bulked segregant microsatellite analysis, with a total progeny of 83 animals (36 'sure dwarf') and 10 parents (none of the parents used twice).

2.2 Blood Samples

Blood samples in EDTA were taken from chickens of all $F_2$ families and their $F_1$, parents and frozen at −80° C. until analysis. DNA from the blood samples was purified using a Puregene DNA isolation kit (Gentra Systems Inc., NC, USA) according to the manufacturers recommendations. DNA was isolated from individual blood samples and from pooled blood samples: Blood pools from 'sure dwarf' animals and from 'sure not dwarf' animals from five families were made (Crooijmans et al., 1996b). DNA concentration from each sample was measured using a GeneQuant RNA/DNA calculator (Pharmacia, Uppsala, Sweden) and diluted in Tris-EDTA (pH=8.0) to a final concentration of 10 µg/ml ($OD_{260}$).

PCR and Gel Electrophoresis

The PCR reactions were performed using a PTC-100–96V Programmable Thermal Controller (MJ Research, Watertown, N. Mex. USA). The reactions were performed in a total volume of 12 µl containing approximately 50 to 100 ng genomic DNA, 1.5 mM $MgCl_2$, 50 mM KCl, 10 mM Tris-HCl (pH=9.0), 1 mM tetramethylammoniumchloride (TMACl), 0.1% Triton X-100, 0.01% gelatin, 200 µM DNTP, 0.25 Unit Goldstar polymerase (Eurogentec S. A., Ougree, Belgium) and 30 ng of each microsatellite primer. The PCR reactions started with 5 minutes at 95° C. and continued with 35 cycles of 30 sec. at 95° C., 45 sec. at 50°–55° C. (depending on microsatellite) and 90 sec. at 72° C., followed by a final elongation of five minutes at 72° C. The amplification products were separated on a 6% denaturing polyacrylamide gel (Sequagel-6, National Diagnostics, Atlanta, Ga., USA) using a Pharmacia Automated Laser Fluorescent (ALF) DNA sequencer. Sizing of the fragments was performed using DNA fragments of known sizes (Pharmacia, Uppsala Sweden) as internal standards and Fragment Manager V 1.2 software was used to analyse the data (Pharmacia).

Bulked Segregant Analysis and Individual Analysis

Initially, 111 microsatellite markers were selected to perform a total genome scan (supplement VI). PCR products of each marker tested on the five pooled DNA samples of the progeny (dwarf/not dwarf) and their parents were analysed and allelic frequencies in the progeny were calculated according to the peak area of the allele. When a parent is heterozygous for a microsatellite marker, it often occurs that the peak area of the one allele is different from the other. Different alleles sometimes have different amplification in PCR. Therefore, peak areas in the progeny have to be adjusted for these different peak areas. Individual progeny samples were tested for markers showing a marked difference in allelic frequencies to determine the exact frequencies of the alleles and to facilitate linkage analysis.

Linkage Analysis

Linkage analysis was performed using CRI-MAP software version 2.4 (Green et al., 1990). A minimum LOD-score ($Log^{10}$ of odds (Ott, 1995)) of three was taken to indicate significant linkage. From a certain number of observations on two microsatellites on a group of animals and their parents, one can count the number of recombinants (i.e. the recombination traction). The LOD-score resembles the $Log^{10}$ likelihood of these two markers being linked divided by the likelihood of no fink-age. A LOD-score higher than 3 is usually regarded as a threshold for significance.

Phenotypic Differences Between Animals

Of all families used in the analysis, both dwarfs and non-dwarf animals were genotyped for the different microsatellites. However, body weight data were available of all progeny of these families. This facilitated analysis of body weight data it combination with microsatellite data. Body weight differences between the 'sure dwarf' and 'probably dwarf/probably non-dwarf'/'sure non-dwarf' animals were determined using the General Linear Model (GLM) procedure of the SAS 6.11 software (SAS. Cary, N.C., USA).

Isolation of (Putative) Chicken HMGI-C Clones from a Genomic Library

The mouse HMGI-C cDNA, subcloned in the Bluescript KS+plasmid (Stratagene, La Jolla, Calif., USA), was obtained from Dr. G. Manfioletti, Dipartimento di Biochemica, Biofisica e Chimica delle Macromolecole, Universita di Trieste, Italia). The plasmid contains a ±1.8 kb insert coding for the HMGI-C and also the $Amp^r$ gene. The insert can be cut out using EcoR1 (5' end) and HindIII (3' end). XL1-Blue E. Coli bacteria were transformed with the plasmid and grown overnight on agar plates containing Amp. Positive clones were isolated and grown overnight in 2 ml LC medium containing Amp. DNA was isolated using the Easyprep system (Pharmacia, Uppsala, Sweden) and after testing the DNA on a 0.8% agarose gel, the HMGI-C cDNA was cut out using. HindIII and EcoRl. Fragments were separated on a 0.8% agarose gel and the cDNA was isolated from the agarose gel. The gel slice was transferred into a punctured. sterile eppendorf tube that had been plugged with approximately 2–3 mm of siliconised sterile glass wool. This tube was put into another eppendorf tube and centrifuged for 10 minutes at 6,000 rpm in a microfuge. The eluate containing the DNA fragment was thus collected in the bottom tube. After precipitation and determination of cDNA concentration using γ fragments with known concentration the fragment was ready for labeling using the Ready-to-go DNA labeling kit ($\alpha$-$^{32}P$-dCTP) (Pharmacia, Uppsala, Sweden).

A commercial chicken genomic library was screened with the mouse HMGI-C probe in order to find the chicken homologue of this murine gene. A genomic library of a male adult Leghorn Liver, cloned in the EMBL3 phage (Clontech cat. #CL1012j, Clontech Inc., Palo Alto, Calif., USA), was used. The library contained $5.9*10^6$ independent clones, with an average insert size of 15 kb (8–22 kb). The exact titre of the library was determined using UB406 E. Coli indicator ceus and appeared to be $5*10^9$ pfu/ml. Now the library was plated out on big petri dishes. To be sure that each genomic clone is represented on the plates, the total coverage should be at least three times the total genome of the chicken ($1,2\times10^9$ bp). Nitro-cellulose filters were drawn and hybridised overnight with the $^{32}P$ radioactive labeled mouse HMGI-C cDNA. Hybridising plaques were detected by autoradiography.

Isolation of Putative Chicken HMGI-C Clones from a Chicken Embryo cDNA Library

The mouse HMGI-C cDNA probe described above was used to screen a cDNA library derived from a 5 day old chicken embryo cloned into the UNI-ZAP vector (Stratagene, La Jolla, Calif., USA). Approximately 100,000 clones were plated out as described above, and nitro-cellulose filters were hybridised with $^{32}P$ radioactive labeled mouse Hmgi-c cDNA. After two more rounds of screening, pure hybridising plaques were used to recover the pBluescript plasmid containing the cDNA insert by using the in vivo excision protocol described by the supplier (Stratagene). Eventually, two different cDNA clones (1400 and 2200 bp insert sizes) were partially sequenced using an automated sequencer (ALF, Pharmacia).

Fish Procedure

Metaphase chromosomes were obtained from cultures of chicken embryo fibroblasts after treatment with a hypotonic solution and fixed in methanol-acetic acid (3:1). The spreads were stained with quinachrin, analyzed by fluorescence microscopy and photographed using a cooled CCD camera. For fluorescence in situ hybridization the LEI146 probe was labeled with biotin-16-dUTP and the HMGI-C probe was labeled with either biotin-16-dUTP or digoxigenin-11-dUTP. The biotinylated probe was detected by subsequent incubation with AvFITC, BioGAA and again AvFITC, and the digoxigenin labeled probe was detected by subsequent incubation with MAdig, RAMTRITC and SWARTRITC. the DNA was counterstained with DAPI. In the pre-photographed spreads the signals were detected by fluorescence microscopy and pictures were taken by a cooled CCD camera. As a result a specific signal for both probes was found on chromosome 1p near the centromere.

Isolation of LEI146 Positive Clones from a Genomic Library

Apart from the screening with the radioactive mouse HMGI-C cDNA, a screening was performed using the LEI146 microsatellite marker. The PCR product was precipitated and labeled using the Ready-to-go DNA labeling kit ($\alpha$-$^{32}$P-dCTP) (Pharmacia, Uppsala, Sweden). Hybridization with the genomic library was carried out as described above.

3. Results

Bulked Segregant Analysis

Of the 111 microsatellite markers selected (see FIG. 2) for the 'total genome scan', 31 were tested using bulked segregant analysis in five different families (Table I). The percentages of the different alleles were estimated for 'dwarf' and 'non-dwarf' pooled progeny samples and their parents and three linked microsatellite markers (MCW112, MCW 43, MCW18; all in linkage group WAU 1) showed a marked difference between 'dwarf' and 'non-dwarf' allele frequencies in the families, which is shown in FIG. 3 and Table II, together with the expected percentages based on uncoupled segregation. Percentages differing more than 25% from the expected values or differing more than 25% between 'dwarfs' and 'non-dwarfs' are shown in bold. Other markers, not linked with the above mentioned ones, occasionally showed allele frequency differences between 'dwarf' and 'non-dwarf' animals bigger than 25%. However, these differences were not consistent in other families (Table III). The results in Table II show differences in four of the five families and for two or three microsatellite markers. Based on this result, it was decided to test $F_1$ and $F_2$ animals individually for MCW43, MCW18 and MCW112 before continuing the 'total genome scan'. Especially the results of MCW43 in families 25/880 and 17/932 suggested linkage with the autosomal dwarfism gene.

Individual Analysis

Individual DNA samples were tested for MCW43, MCW18 and MCW 112. A total of 83 animals from 5 families, of which 36 were dwarfs, were analysed. Six animals, 7.2%, (two dwarfs) appeared to have a microsatellite profile that did not match with the parental profile and these animals were excluded from further analysis. Recombination fractions and LOD-scores were calculated using CRI-MAP software. Dwarfs were genotyped as homozygous recessives (adw/adw) and non-dwarfs as carriers of at least one copy of the wild-type allele (* Adw-). CRI-MAP' results are shown in Table IV. The significant LOD-scores (LOD-scores >3.00) supported the initial hypothesis based on the bulked segregant data on the location of the gene. Based on these data the gene is located between MCW43 and MCW18 on linkage group WAU1 (chromosome 1), which is the same as E1 (East Lansing International reference family) and C15 (Compton International reference family). However, the big gap between the two microsatellite markers (44 cM) made it necessary to analyse more data, in order to confirm this result and to better specify the location of the Adw/adw. gene. First, the effect of adding more families was computed using CRI-MAP'. Each family was used twice in one CRI-MAP run, resulting in ten families with a progeny of 144 animals. The results of this analysis, showed in Table V, revealed that is would be useful to test more families. A quadratic increase of LOD scores was observed, which results in more significant linkage between the microsatellites and the QTL. Secondly, it was also decided to test additional microsatellite markers linked with MCW43 and MCW18, in order to further specify the location of the Adw/adw. gene on the linkage map. Based on the results of Table V it was decided to test more families segregating for the autosomal dwarf gene. Seven additional families were incorporated in the study. All parents were used in only one of the 12 crosses[1]. Microsatellite analysis was now carried out on the 24 parents and 157 animals from the progeny of these parents (see Table VI). Of these 157 animals, 12 (8%) animals appeared to have a genotype that did not match with the parental phenotype (an additional six animals plus the six already mentioned).

1) Data from Euribrid BV suggested that cock 25 was used twice (hen 880 and 887), but microsatellite analysis showed that the cock used for hen 880 was not the same cock as the one used for hen 887. Because of the Organisation of the blood sample batches, cock—hen—progeny per family it is reasonable to assume that a mistake occurred in the data.

Because three animals from family 4 (24/877; 5 animals) had to be excluded from the data set, it was decided to exclude the whole family for microsatellite analysis. It is reasonable to suspect that one of the parental blood samples did not originate from the right parent.

Testing of additional markers linked with MCW18 and MCW43

A test panel including 7 microsatellite markers: ADL307, ADL234, MCW43, MCW18, ADL150, MCW112 and LMU 62 was analysed. Recent research revealed that microsatellite marker LMY 105 is located between MCW43 and MCW18 (M. A. M. Groenen, unpublished results), so this microsatellite marker was also included in the test panel.

Figure 4A:
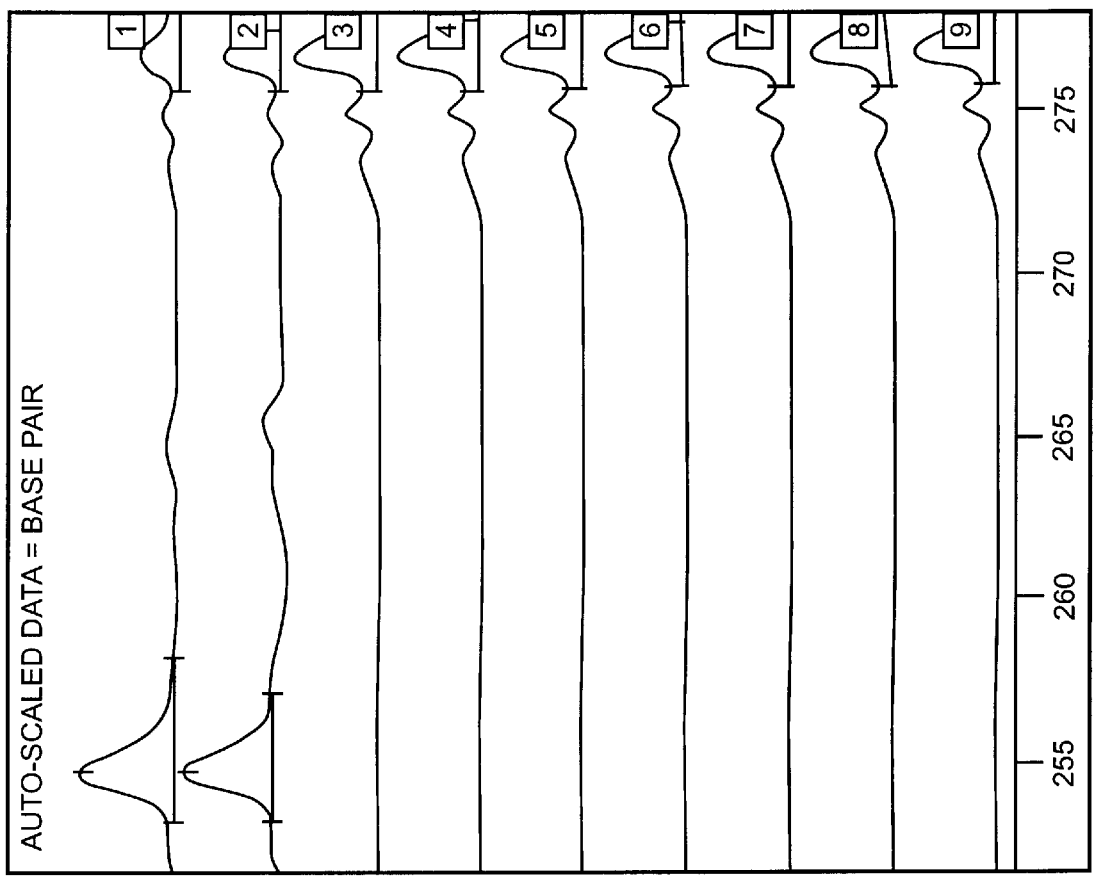
FIG. 4A illustrates the differences in allelic distribution for LMU 105 for family 17/932: curve 1 is derived from the male parent, curve 2 is derived from the female parent, that are both heterozygous for this microsatellite marker (255 bp, 276 bp alleles. Curves 3–9 illustrate the Dwarf progeny, all carrying two 276 bp alleles.
Figure 4B:
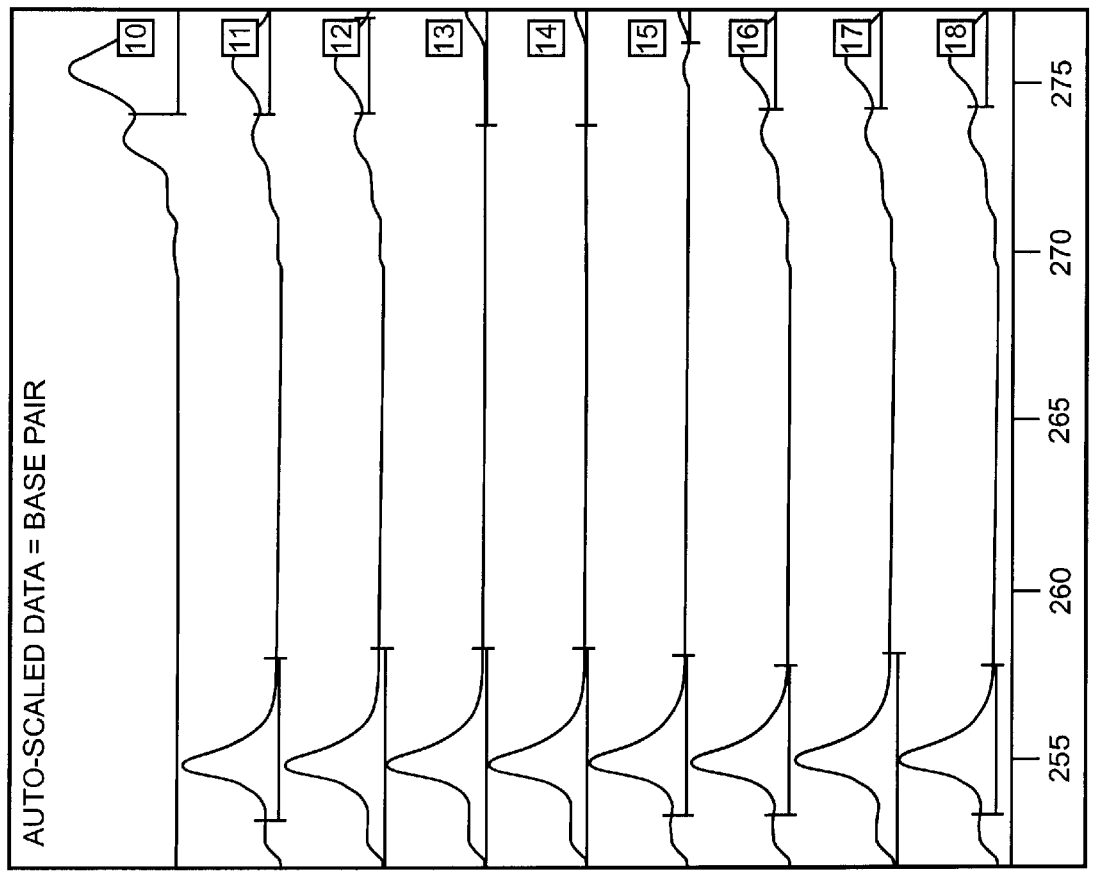
FIG. 4B illustrates the differences in allelic distribution for LMU 105 for family 17/932, as for FIG. 4A. Curve 10 illustrates another "dwarf", curves 11–18 show the "non-dwarfs", either carrying two copies of the 255 bp allele or one copy of the 255 bp allele and one copy of the 276 bp allele. The trait is recessive, so heterozygous animals cannot be separated phenotypically from homozygous animals. The 276 bp allele is clearly coupled to the adw allele, so based on these figures, it is to be expected that only the animals in 13–15 have the Adw/Adw genotype. However, the recombination fraction is still 0.03, so there remains a possibility of crossing over.

FIG. 4 shows individual results for microsatellite LEI146, revealing strong linkage with the Adw/adw gene. All miccrosatellite data were again analysed using CRI-MAP software. Table VII shows the number of informative meioses for each microsatellite marker. Since blood samples of the $F_0$ generation were not available, there were no phase-known meioses. LOD-scores and recombination fractions are shown in Table VIII. Based on the WAU linkage map and the present data, a linkage map was build using the CRI-MAP options build and flips. The ordered loci were analysed according to their order on the WAU linkage map. All individual data were checked using the chrompic option, which determines the phase of the different alleles. Microsatellite data from individuals showing double crossovers on a short linkage distance were checked.

Finally, the most likely location of the adw locus was calculated and results are shown in Table IX. Because the WAU linkage map (supplement M) is based on more informative meioses (i.e. more data; full sib families, 480 animals) than the present study, the microsatellites were put in the WAU locus order in the CRI-MAP option build, although this was not the most likely order according to the dwarf data.

The recombination fraction between LEI146 and adw equals 0.03, LOD-score 23.62 (see Table VIII and Table IX). The Log10 likelihood of adw being located between MCW43 and LMU 105 is –207.67, whereas the likelihood of adw being located between LEI146 and MCW18 equals –205.34, a $10^{2.33}$ difference in absolute likelihood. When CRI-MAP calculated the linkage map on itself (without knowing the WAU linkage order) the Adwladw locus was mapped on exactly the same place: closely to LEI146.

Screening Genomic Library with a Mouse HMGI-c c-DNA and a Chicken LEI146 Orobe

The linkage between Ad/adw and LEI146 resulted in localisation of this gene on chromosome I between MCW43 and MCW18. Interestingly, the chicken Igf-I gene is also located between these two microsatellite markers. The Igf-I gene is located on human chromosome 12 (12q22–12q24. 1: MIM gene map, The Jackson Laboratory Mouse Genome Informatics) and on mouse chromosome 10. In both species, the gene coding for the HMGI-c protein is also located on these chromosomes: on human chromosome 12, position 12q15 (MIM gene map) and on mouse chromosome 10, approximately 25 cM from the Igf-I gene. It was decided to screen a chicken genomic library with a mouse HMGI-C cDNA probe. The library was also screened with a LEI146 probe in order to be able to use a genomic clone of known location for Fluorescent In Situ Hybridisation (FISH) in combination with the putative chicken Hmgi-c genomic clone. From the screening of the genomic library, 10 positive clones for LEI146 were isolated. For HMGI-C, 32 clones were isolated. In the second screening, further purification of the clones was carried out. Plaques from the LEI146 probe gave much better signals than the ones from HMGI-C-probe. LEI146 is a homologous chicken probe, and HMGI-C is a heterologous mouse probe.

Results from Sequence Analysis of the Isolated Chicken HMGI-C Clones

Southern blots derived from the DNA of 5 of the HMGI-C positive genomic clones, digested with a number of restriction enzymes, were hybridised with the mouse HMGI-C cDNA. In two of the 5 clones, specific fragments hybridised to the mouse HMGI-C probe. From one of the genomic clones, the hybridising PstI fragments (0.9 and 1.1 Kbp) and the hybridising HindII fragment (1.4 Kbp) were subcloned into pBluescript, which resulted in the genomic subclones HP2, HP3 and HH1. The inserts of these genomic subclones were partially sequenced with both the reverse and forward sequencing primers. The resulting sequence (see FIG. 5) clearly showed that the isolated chicken gene belonged to the HMG family of genes, and that it contained at least part of intron 4 and the complete exon 5. Moreover, since the first 100 bp of the 3'non-coding region of the mRNA (present on exon 5), showed 80% sequence similarity to the same region in the human and mouse gene, it is very likely that the cloned chicken gene indeed is the HMGI-C gene.

Figure 6:
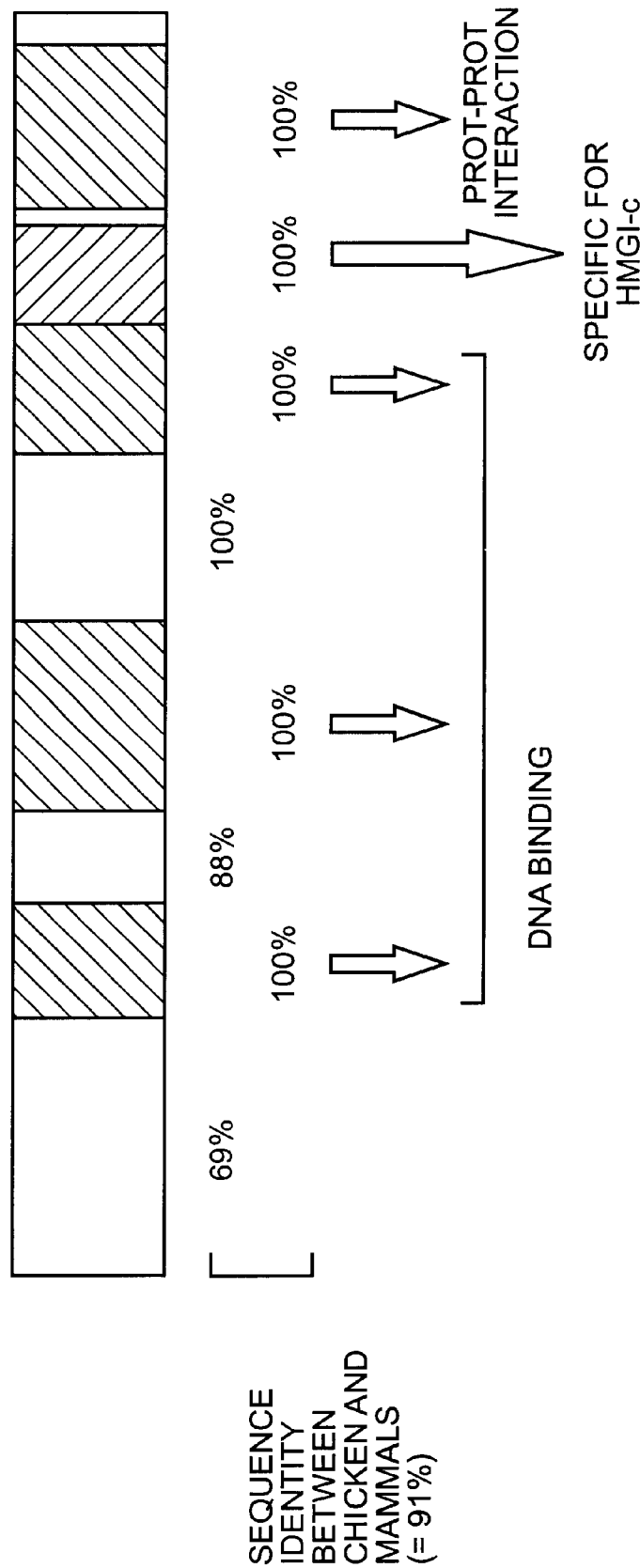
FIG. 6 illustrates the homology between chicken and mammal of the HMGI-c gene.

Screening of the chicken embryo cDNA library resulted in a very large number of positively hybridising clones, indicating that the gene is highly expressed in embryonic tissue. Two of the positive clones, HCC4 and HCC3 (with insert sizes of 1.1 and 2.2 Kbp respectively) were selected and partially sequenced. The resulting sequence (FIG. 1) showed that both clones were derived from the same gene as the genomic clone. Alignment of the cDNA sequence and its derived-aminoacid sequence with those of the HMGI-c gene of mouse and man, clearly showed that the cloned gene indeed was the chicken HMGI-C gene. Similar as the mammalian HMG family members, this gene coded for a putative DNA binding protein with highly conserved DNA binding domains and a highly conserved domain probably involved in protein-protein recognition. In addition, similar as in HMGI-c in mammals, the chicken protein has an extra amino acid motive (between the last DNA binding motive and the pro-prot interaction motive, see FIG. 6) that is only found in the HMGI-c protein, and which is absent from the other HMG family members. Particularly, this protein motive shows that we have cloned the chicken HMGI-C gene rather than another highly conserved family member. Assignment of the Chicken HMGI-c Gene and Marker LEI146 to a Chromosomal Segment on Chromosome 1p To enable physical mapping of the microsatellite marker LEI146 using Fluorescent in situ hybridisation (FISH), genomic fragments of this marker were also isolated from a chicken genomic library, and partially sequenced to identify true positive genomic clones for this marker. Both the genomic lambda clone for the chicken Hmgi-c gene and the genomic lambda clone for marker LMU146 were fluorescently labeled and hybridised to meta-phase chromosome spreads of the chicken in two seperate FISH experiments. Both clones map to a similar region on chromosome 1p, close to the centromere. Subsequently, in a double labeling FISH experiment it was confirmed that both loci are located very close on the same region of chromosome 1p.

Results from Statistical Analysis of Chicken Body Weight Data

Animals were bred in four time periods, resulting from 11 parental crosses. Based on the original weight records, a data set containing all animals from the families used was made (see Table X). It should be noticed that the animals actually analysed for microsatellite markers are found in Table VI. Dwarf animals not analysed are animals with missing blood samples. Only a selection of 'heavy' animals (i.e. the 'sure non-dwarf' animals) was used for microsatellite analysis.

Cocks and hens were separated as being 'dwarf' (24%) or 'non-dwarf' (76%); the 'probably dwarf' animals were included in the second group. The statistical model used was:

$$\text{weight}_{abcd} = \mu + \text{family}_a + \text{period}_b + \text{sex}_c + \text{phenotype}_d + \text{error}_{abcd}$$

| | |
|---|---|
| weight | Body weight in grams of progeny d |
| family | Family a (1–11) in which progeny d is born |
| period | Breeding period b (1–4) in which progeny d is born |
| sex | Sex c (Male/Female) |
| phenotype | Phenotype d (Dwarf/Non-dwarf) |

This model proved to be the best model, since it only includes variables with significant effects (p<0.05). All interaction terms were tested and non-significant (interaction) terms were stepwise deleted from the model resulting in the present model. of the 363 animals in the data set, only 342 could be used due to missing values: 18 due to missing sex and 3 due to missing weight. In the model, weight is a variable explained by the fixed family, period, sex and phenotype effects and an error term. Results are in Table XI. The SAS General Linear Model estimates an overall mean ($\mu$=994.5 g) and a Lsmean for each variable. of course, the goal of this procedure was to determine the 'phenotype' effect: to show the significant difference between 'dwarf and 'non-dwarf' chicken. This is possible by correcting the observation on weight for estimated Lsmean for family, period and sex.

$$\text{Weight}_{abcd} - \text{Lsmean Family}_a - \text{Lsmean Period}_b - \text{Lsmean Sex}_c \mu + \text{Lsmean Phenotype}_d + \text{error}_{abcd} \quad (2)$$

Figure 7:
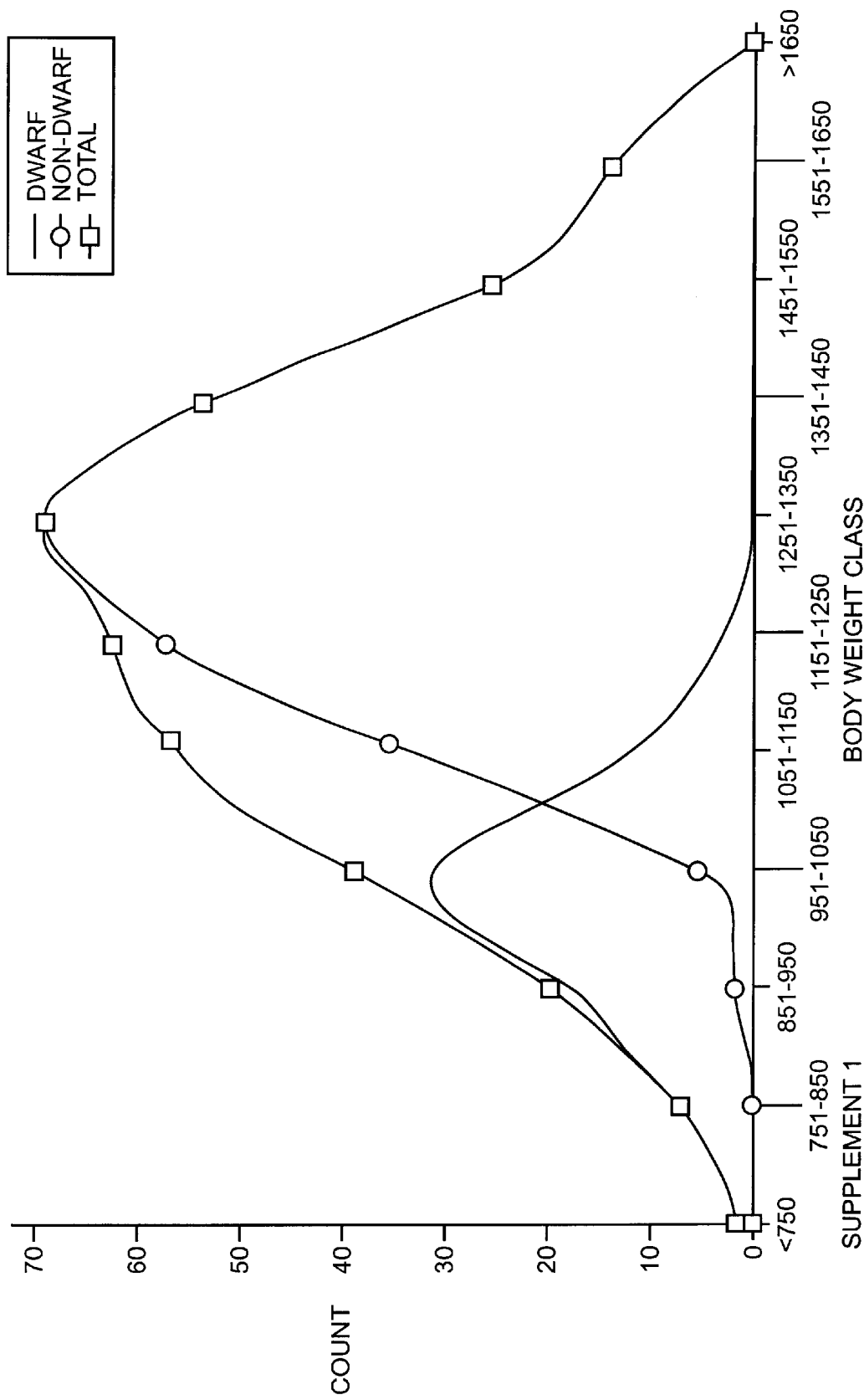
FIG. 7 illustrates the distribution of body weights after correction for sex, period and family effects. Curves are labeled as follows: Dwarf (——); Non-Dwarf (—o—); Total (—□—).
Figure 8:
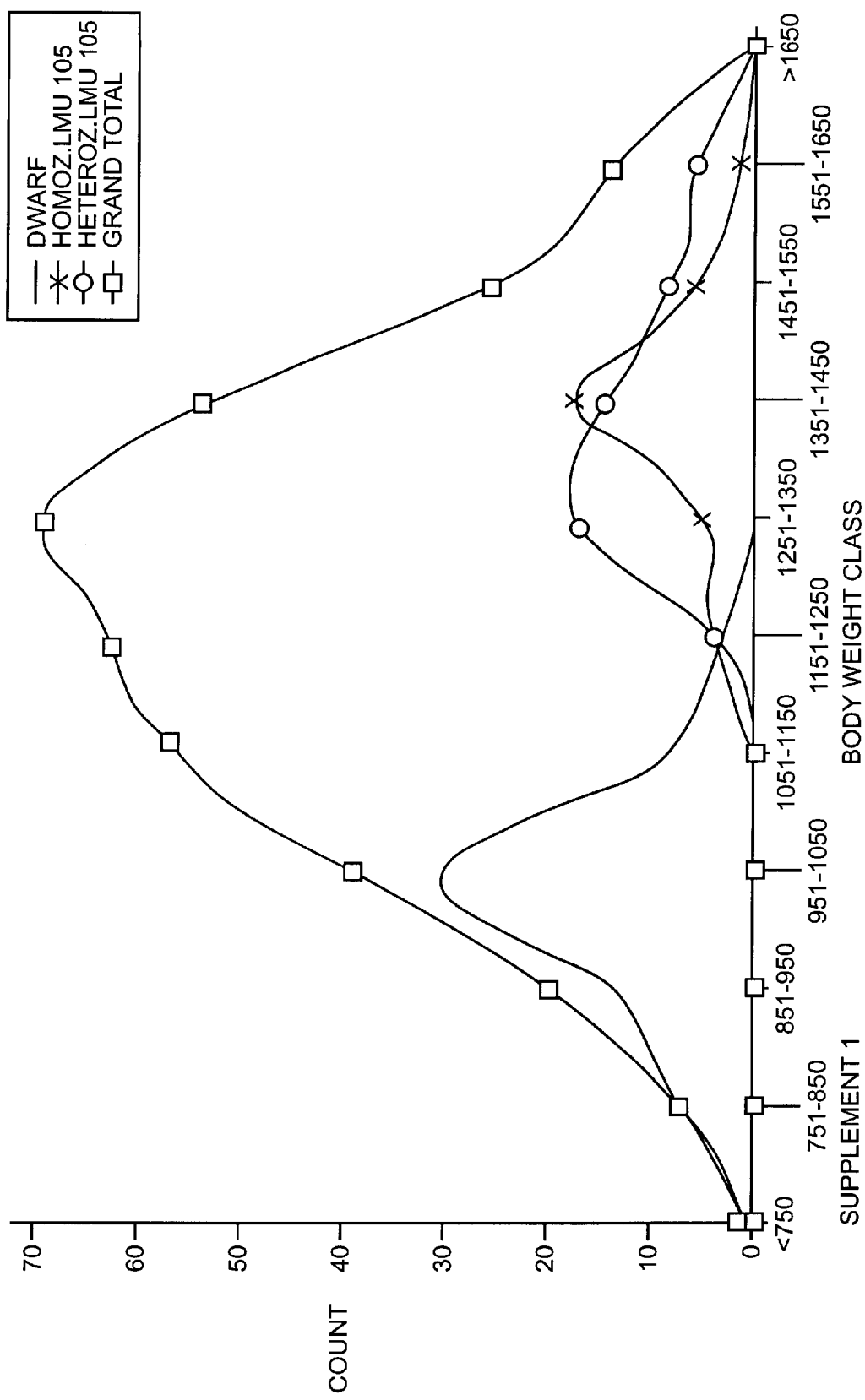
FIG. 8 illustrates a comparison of LMU 105 genotypes and body weights from the non-dwarf animals. Curves are labeled as follows: Dwarf (—); Heterozyg. (—o—); Grand total (—□—); Homozyg. (—X—).

The corrected weights were calculated and plotted in histograms (FIG. 7) These corrected weights can be combined with phenotypic data. FIG. 7 shows the differences in body weight between 'dwarfs' and 'non-dwarfs' after correction for sex, family and period effects. The mean of the corrected 'dwarf body weights, 989.9 g, differs significantly from the 'non-dwarf' body weights, 1297.4 g (p<0.001, one-sided Student's t-test with unequal variance, equal variance of the two groups was tested with a Fisher-test, p<0.01). The right-end of the distribution in FIG. 7 does suggests a difference between heterozygous and homozygous dominant animals: there seems to be a heavy subgroup of 'non-dwarfs', which might result from the double dominant animals. The dominant allele in the heterozygous animals might not have a full penetrance. This can only be confirmed by analysing all animals and subsequent statistical analysis. Since LEI146 is strongly linked to Adw/adw and because the 276 bp allele is linked to the adw allele in all families, it is useful to compare weights of the three possible LEI146 genotypes. The heterozygous animals, animals carrying one copy of the 276 bp allele, might have lower body weights than the animals not carrying the 276 bp allele. Indeed, FIG. 8 shows a difference between these animals. However, the corrected body weights of these animals do not differ significantly in a Student's t-test (p=0.45 in a one-sided test with equal variance, again confirmed with a Fisher-test). It should be noted that LMU105 has a recombination fraction of 0.03, which means that 3 out of 100 animals are recombinants.

Individual Linkage Analysis

Figure 9:
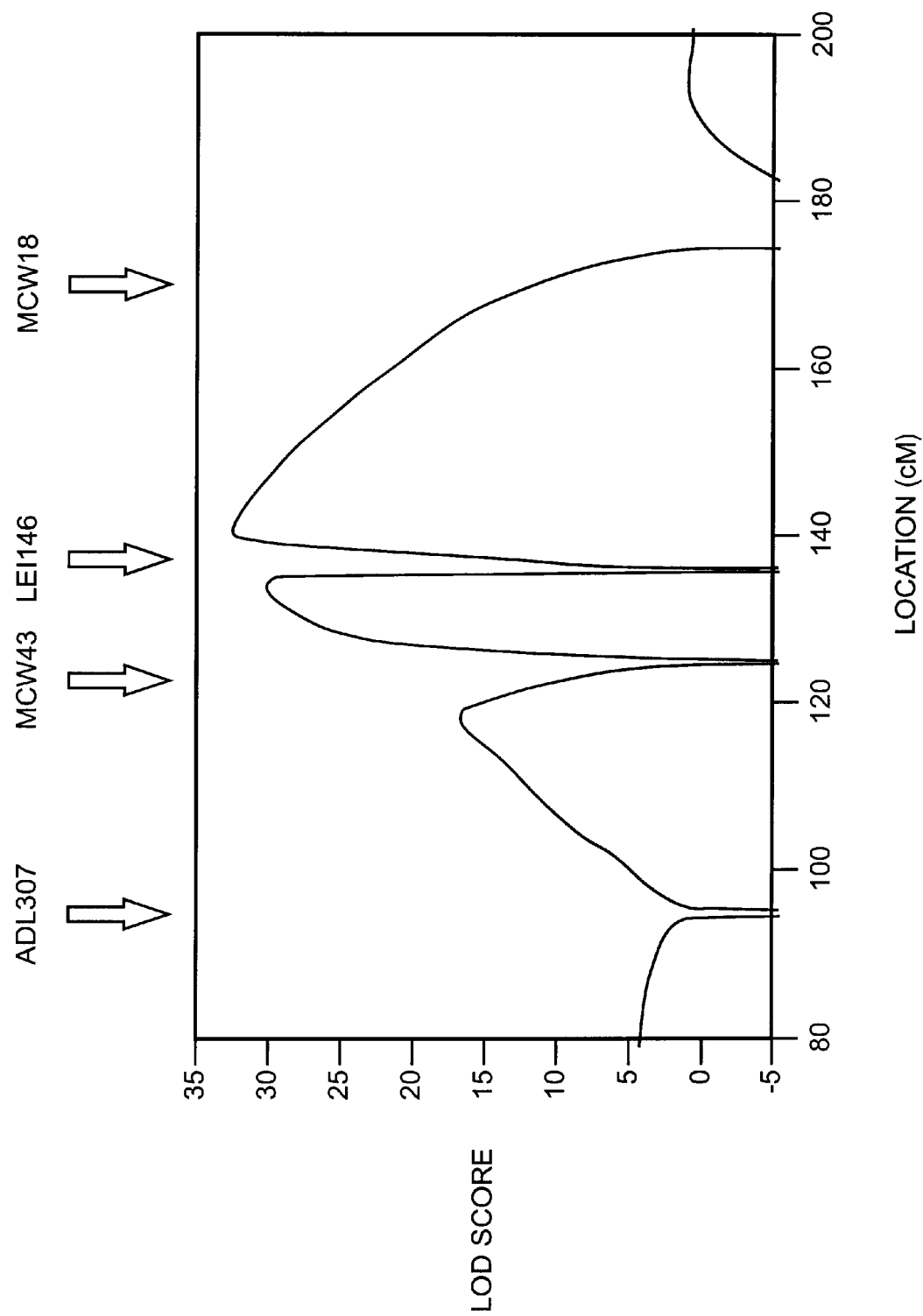
FIG. 9 illustrates a comparison of LOD scores (Y axis) verses Location in centi Morgan (X axis) for ADL 307, MCW43, LEI146 and MCW18.

In order to verify the results from the bulked segregant analysis experiment and in order to obtain a more accurate estimation of the location of the adw locus on the genetic linkage map, DNA samples from 145 dwarf and non-dwarf chickens were subjected to individual linkage analysis. Five microsatellite markers (MCW43, MCW18, ADL307, LEI171, LEI146), all being located in the region of the adw locus, were analyzed. One of these markers (LEI146) was located in the region between MCW43 and MCW18. Using two point analysis, positive linkage with the adw locus was found for all markers except ADL307 and LEI71, the recombination fraction between LEI146 and the adw locus being as low as 0.03 ($LOD_{linkage}$ score=31.98). A multipoint analysis revealed the most likely position of the adw locus with respect to the markers present on linkage group WAU1 (FIG. 9).

TABLE I

Families used for bulked segregant analysis

| Family | Parents | | Progeny Dwarf | | | Progeny Non-dwarf | | | Total |
|---|---|---|---|---|---|---|---|---|---|
| | Cock | Hen | Cocks | Hens | Unknown[1] | Cocks | Hens | Unknown[1] | |
| 1 | 20 | 858 | 4 | 2 | 0 | 8 | 0 | 0 | 14 |
| 2 | 25 | 880 | 2 | 5 | 0 | 8 | 2 | 0 | 17 |
| 3 | 15 | 923 | 3 | 4 | 0 | 6 | 3 | 2 | 18 |
| 4 | 17 | 932 | 3 | 5 | 0 | 4 | 6 | 0 | 18 |
| 5 | 6 | 969 | 3 | 5 | 0 | 5 | 2 | 1 | 16 |
| | | Total | 15 | 21 | 0 | 31 | 13 | 3 | 83 |

[1]unknown sex

TABLE II

Percentages of different alleles for MCW43, MCW18 and MCW112 determined using bulked segregant analysis

| Family | | 15/923 | | 25/880 | | | 6/969 | | |
|---|---|---|---|---|---|---|---|---|---|
| Number of Animals | | 18 Total, 7 Dwarf | | 17 Total, 7 Dwarf | | | 16 Total, 8 Dwarf | | |
| Microsatellite | | Allele 1 | Allele 2 | Allele 1 | Allele 2 | | Allele 1 | Allele 2 | |
| MCW43 | Cock | 130 bp | 134 bp | 130 bp | 134 bp | | 130 bp | 134 bp | |
| | Hen | 134 bp | 134 bp | 130 bp | 134 bp | | 130 bp | 134 bp | |
| | | 130 bp | 134 bp | 130 bp | 134 bp | | 130 bp | 134 bp | |
| | Non-dwarf | 50% | 50% | 45% | 55% | | 59% | 41% | |
| | Dwarf | 31% | 69% | 0% | 100% | | 42% | 58% | |
| | Expected | 25% | 75% | 50% | 50% | | 50% | 50% | |
| MCW18 | Cock | 225 bp | 233 bp | 219 bp | 233 bp | | 231 bp | 233 bp | |
| | Hen | 225 bp | 233 bp | 225 bp | 233 bp | | 225 bp | 233 bp | |
| | | 225 bp | 233 bp | 219 bp | 225 bp | 233 bp | 225 bp | 231 bp | 233 bp |
| | Non-dwarf | 58% | 42% | 51% | 26% | 22% | 34% | 38% | 28% |
| | Dwarf | 20% | 80% | 13% | 2% | 85% | 15% | 40% | 46% |
| | Expected | 50% | 50% | 25% | 25% | 50% | 25% | 25% | 50% |
| MCW112 | Cock | 274 bp | 276 bp | 272 bp | 274 bp | | 261 bp | 274 bp | |
| | Hen | 274 bp | 276 bp | 261 bp | 276 bp | | 261 bp | 276 bp | |
| | | 274 bp | 276 bp | 261 bp | 272 bp | 274 bp | 276 bp | 261 bp | 274 bp | 276 bp |
| | Non-dwarf | 44% | 56% | 29% | 32% | 12% | 28% | 35% | 24% | 41% |
| | Dwarf | 68% | 32% | 39% | 14% | 32% | 15% | 50% | 29% | 21% |
| | Expected | 50% | 50% | 25% | 25% | 25% | 25% | 50% | 25% | 25% |
| Family | | 20/858 | | 17/932 | | | | | |
| Number of Animals | | 14 Total, 6 Dwarf | | 18 Total, 8 Dwarf | | | | | |
| Microsatellite | | Allele 1 | Allele 2 | Allele 1 | Allele 2 | | | | |
| MCW43 | Cock | 130 bp | 134 bp | 130 bp | 134 bp | | | | |
| | Hen | 130 bp | 134 bp | 130 bp | 134 bp | | | | |

TABLE II-continued

Percentages of different alleles for MCW43, MCW18 and MCW112 determined using bulked segregant analysis

|  |  | 130 bp | 134 bp | 130 bp | 134 bp |  |  |
|---|---|---|---|---|---|---|---|
|  | Non-dwarf | 61% | 39% | 45% | 55% |  |  |
|  | Dwarf | 22% | 78% | 0% | 100% |  |  |
|  | Expected | 50% | 50% | 50% | 50% |  |  |
| MCW18 | Cock | 227 bp | 233 bp | 231 bp | 233 bp |  |  |
|  | Hen | 225 bp | 233 bp | 219 bp | 233 bp |  |  |
|  |  | 225 bp | 227 bp | 233 bp | 219 bp | 231 bp | 233 bp |
|  | Non-dwarf | 37% | 37% | 26% | 33% | 34% | 33% |
|  | Dwarf | 0% | 9% | 91% | 10% | 30% | 60% |
|  | Expected | 25% | 25% | 50% | 25% | 25% | 50% |
| MCW112 | Cock | 261 bp | 274 bp |  | 261 bp | 274 bp |  |
|  | Hen | 261 bp | 276 bp |  | 261 bp | 274 bp |  |
|  |  | 261 bp | 274 bp | 276 bp | 261 bp | 274 bp |  |
|  | Non-dwarf | 43% | 28% | 30% | 52% | 48% |  |
|  | Dwarf | 48% | 52% | 0% | 25% | 75% |  |
|  | Expected | 50% | 25% | 25% | 50% | 50% |  |

TABLE III

Percentages of different alleles for MCW68, MCW109 and MCW200 determined using bulked segregant analysis

| Family | 15/923 | | | 25/880 | | | | 6/969 | | | |
|---|---|---|---|---|---|---|---|---|---|---|---|
| Number of Animals | 18 Total, 7 Dwarf | | | 17 Total, 7 Dwarf | | | | 16 Total, 8 Dwarf | | | |
| Microsatellite | Allele 1 | Allele 2 | | Allele 1 | Allele 2 | | | Allele 1 | Allele 2 | | |
| MCW68 Cock | 171 bp | 196 bp | | 174 bp | 181 bp | | | 174 bp | 177 bp | | |
| Hen | 181 bp | 181 bp | | 171 bp | 196 bp | | | 171 bp | 181 bp | | |
|  | 171 bp | 181 bp | 196 bp | 171 bp | 174 bp | 181 bp | 196 bp | 171 bp | 174 bp | 177 bp | 181 bp |
| Non-dwarf | 21% | 59% | 20% | 30% | 38% | 11% | 20% | 32% | 15% | 37% | 17% |
| Dwarf | 49% | 51% | 0% | 35% | 31% | 20% | 15% | 22% | 36% | 15% | 27% |
| Expected | 25% | 50% | 25% | 25% | 25% | 25% | 25% | 25% | 25% | 25% | 25% |
| MCW109 Cock | 132 bp | 132 bp | | 132 bp | 155 bp | | | 153 bp | 155 bp | | |
| Hen | 132 bp | 155 bp | | 132 bp | 155 bp | | | 134 bp | 157 bp | | |
|  | 132 bp | 155 bp | | 132 bp | 155 bp | | | 134 bp | 153 bp | 155 bp | 157 bp |
| Non-dwarf | 69% | 31% | | 61% | 39% | | | 21% | 22% | 30% | 26% |
| Dwarf | 66% | 34% | | 49% | 51% | | | 13% | 17% | 38% | 32% |
| Expected | 75% | 25% | | 50% | 50% | | | 25% | 25% | 25% | 25% |
| MCW200 Cock | 240 bp | 240 bp | | 240 bp | 248 bp | | | 238 bp | 258 bp | | |
| Hen | 249 bp | 258 bp | | 240 bp | 248 bp | | | 238 bp | 248 bp | | |
|  | 240 bp | 249 bp | 258 bp | 240 bp | 248 bp | | | 238 bp | 248 bp | 258 bp | |
| Non-dwarf | 66% | 20% | 14% | 78% | 22% | | | 39% | 36% | 25% | |
| Dwarf | 65% | 20% | 15% | 58% | 42% | | | 55% | 34% | 11% | |
| Expected | 50% | 25% | 75% | 75% | 25% | | | 50% | 25% | 25% | |
| Family | 20/858 | | | 17/932 | | | | | | | |
| Number of Animals | 14 Total, 6 Dwarf | | | 18 Total, 8 Dwarf | | | | | | | |
| Microsatellite | Allele 1 | Allele 2 | | Allele 1 | Allele 2 | | | | | | |
| MCW68 Cock | 177 bp | 196 bp | | 181 bp | 181 bp | | | | | | |
| Hen | 172 bp | 1896 bp | | 181 bp | 196 bp | | | | | | |
|  | 172 bp | 177 bp | 196 bp | 181 bp | 196 bp | | | | | | |
| Non-dwarf | 29% | 44% | 27% | 81% | 19% | | | | | | |
| Dwarf | 39% | 7% | 54% | 92% | 8% | | | | | | |
| Expected | 25% | 25% | 50% | 75% | 25% | | | | | | |

TABLE III-continued

Percentages of different alleles for MCW68, MCW109 and MCW200 determined using bulked segregant analysis

| MCW109 | Cock | 132 bp | 141 bp | | 151 bp | 153 bp | | | |
|---|---|---|---|---|---|---|---|---|---|
| | Hen | 134 bp | 155 bp | | 132 bp | 155 bp | | | |
| | | 132 bp | 134 bp | 141 bp | 155 bp | 132 bp | 151 bp | 153 bp | 155 bp |
| | Non-dwarf | 26% | 12% | 39% | 23% | 30% | 15% | 39% | 22% |
| | Dwarf | 67% | 5% | 7% | 21% | 35% | 26% | 23% | 22% |
| | Expected | 25% | 25% | 25% | 25% | 25% | 25% | 25% | 25% |
| MCW200 | Cock | 246 bp | 246 bp | | | 238 bp | 248 bp | | |
| | Hen | 238 bp | 238 bp | | | 238 bp | 238 bp | | |
| | | 238 bp | 246 bp | | | 238 bp | 248 bp | | |
| | Non-dwarf | 62% | 38% | | | 83% | 17% | | |
| | Dwarf | 70% | 30% | | | 91% | 10% | | |
| | Expected | 50% | 50% | | | 75% | 25% | | |

TABLE IV

CRI-MAP results of individual analysis of family 1–5.

| Coupling between: | recombination fraction | LOD-score |
|---|---|---|
| MCW43-Adw/adw. | 0.10 | 6.65 |
| MCW18-Adw/adw. | 0.19 | 3.39 |
| MCW112-MCW18 | 0.09 | 19.90 |

TABLE V

CRI-MAP results of individual analysis of family 1–5, each family incorporated tvace in the data set.

| Coupling between: | recombination fraction | LOD-score |
|---|---|---|
| MCW43-Adw/adw | 0.10 | 13.10 |
| MCW18-Adw/adw | 0.19 | 6.78 |
| mcw18-MCW43 | 0.28 | 4.61 |
| MCW112-Adw/adw | 0.21 | 5.60 |
| MCW112-MCW18 | 0.09 | 39.81 |

TABLE VII

Number of informative meioses for individuals all families.

| Locus | Number of meioses |
|---|---|
| Adw/adw | 126 |
| ADL307 | 102 |
| ADL234 | 105 |
| MCW43 | 255 |
| LEI146 | 286 |
| MCW18 | 284 |
| ADL150 | 252 |
| MCW112 | 253 |
| LMU 62 | 264 |

TABLE VI

Families used for individual analysis

| | Parents | | Progeny Dwarf | | | Progeny Non-dwarf | | | |
|---|---|---|---|---|---|---|---|---|---|
| Family | Cock | Hen | Cocks | Hens | Unknown[1] | Cocks | Hens | Unknown[1] | Total |
| 1 | 19 | 853 | 2 | 2 | 0 | 3 | 3 | 0 | 10 |
| 2 | 20 | 858 | 4 | 2 | 0 | 8 | 0 | 0 | 14 |
| 3 | 23 | 873 | 2 | 3 | 0 | 3 | 3 | 0 | 11 |
| 4 | 24 | 877 | 3 | 0 | 0 | 1 | 1 | 0 | 5 excl. |
| 5 | 25 | 880 | 2 | 5 | 0 | 8 | 2 | 0 | 17 |
| 6 | 225 | 887 | 1 | 2 | 0 | 3 | 0 | 1 | 7 |
| 7 | 10 | 898 | 2 | 5 | 0 | 2 | 5 | 0 | 14 |
| 8 | 15 | 923 | 3 | 4 | 0 | 6 | 3 | 2 | 18 |
| 9 | 17 | 932 | 3 | 5 | 0 | 4 | 6 | 0 | 18 |
| 10 | 1 | 941 | 2 | 6 | 0 | 3 | 6 | 0 | 17 |
| 11 | 2 | 946 | 1 | 4 | 0 | 3 | 2 | 0 | 10 |
| 12 | 6 | 969 | 3 | 5 | 0 | 5 | 2 | 1 | 16 |
| | | Total | 28 | 43 | 0 | 49 | 33 | 4 | 157 |

[1]unknown sex

TABLE VIII

CRI-MAP results of individual analysis of all families.

| Coupling between: | recombination fraction | LOD-score |
|---|---|---|
| MCW43-Adw/adw. | 0.12 | 10.58 |
| LEI146-Adw/adw. | 0.03 | 23.62 |
| MCW18-Adw/adw. | 0.21 | 3.82 |
| MCW112-Adw/adw | 0.23 | 3.23 |
| ADL234-Adw/adw. | 0.11 | 4.33 |
| MCW43-ADL307 | 0.15 | 5.47 |
| LEI146-MCW43 | 0.07 | 31.69 |
| MCW18-MCW43 | 0.28 | 3.66 |
| MCW18-LEI146 | 0.27 | 5.12 |
| ADL150-LEI146 | 0.29 | 3.55 |
| ADL150-MCW18 | 0.04 | 39.90 |
| MCW112-LEI146 | 0.30 | 3.27 |
| MCW112-MCW18 | 0.04 | 40.70 |
| MCW112-ADL150 | 0.01 | 54.07 |
| LMU 62-MCW18 | 0.24 | 8.59 |
| LMU 62-ADL150 | 0.19 | 11.23 |
| LMU 62-MCW112 | 0.21 | 9.73 |
| ADL234-MCW43 | 0.05 | 13.86 |
| ADL234-LEI146 | 0.09 | 10.66 |

TABLE IX

Linkage maps as calculated from CRI-MAP.

| Sex-averaged map Microsatellite | recomb.fraction | Kosambi cM | |
|---|---|---|---|
| ADL307 | 0.10 | 10.30 | 0.00 |
| ADL234 | 0.04 | 4.00 | 10.30 |
| MCW43 | 0.07 | 7.00 | 14.40 |
| LEI146 | 0.27 | 30.4 | 21.40 |
| MCW18 | 0.05 | 4.70 | 51.70 |
| AD L50 | 0.01 | 1.30 | 56.40 |
| MCW112 | 0.22 | 23.50 | 57.70 |
| LMU 62 | | | 81.20 |

| Sex-specific maps Microsatellite | Female recomb. fraction | Female Kosambi cM | Male recomb. fraction | Male Kosambi cM |
|---|---|---|---|---|
| ADL307 | | 0.00 | | 0.00 |
| | 0.07 | 7.50 | 0.20 | 21.70 |
| ADL234 | | 7.50 | | 21.70 |
| | 0.02 | 2.10 | 0.80 | 7.60 |
| MCW43 | | 9.60 | | 29.30 |
| | 0.08 | 8.00 | 0.06 | 5.70 |
| LEI146 | | 17.60 | | 35.00 |
| | 0.27 | 30.70 | 0.27 | 29.90 |
| MCW18 | | 48.30 | | 64.80 |
| | 0.03 | 3.00 | 0.06 | 6.40 |
| AD L50 | | 51.30 | | 71.20 |
| | 0.00 | 0.00 | 0.02 | 2.40 |
| MCW112 | | 51.30 | | 73.70 |
| | 0.27 | 30.40 | 0.17 | 18.10 |
| LMU 62 | | 81.60 | | 91.70 |

TABLE X

Families used for statistical analysis (SAS)

| | Parents | | Progeny Dwarf | | | Progeny Non-dwarf | | | |
|---|---|---|---|---|---|---|---|---|---|
| Family | Cock | Hen | Cocks | Hens | Unknown[1] | Cocks | Hens | Unknown[1] | Total |
| 1 | 19 | 853 | 4 | 2 | 0 | 16 | 14 | 0 | 36 |
| 2 | 20 | 858 | 5 | 6 | 0 | 13 | 11 | 1 | 36 |
| 3 | 23 | 873 | 2 | 5 | 0 | 12 | 12 | 1 | 32 |
| 4 | 25 | 880 | 2 | 6 | 1 | 14 | 8 | 2 | 33 |
| 5 | 225 | 887 | 1 | 4 | 0 | 11 | 15 | 4 | 35 |
| 6 | 10 | 889 | 2 | 5 | 0 | 10 | 15 | 3 | 35 |
| 7 | 15 | 923 | 4 | 5 | 0 | 10 | 17 | 1 | 37 |
| 8 | 17 | 932 | 5 | 6 | 0 | 8 | 14 | 1 | 34 |
| 9 | 2 | 941 | 3 | 6 | 0 | 7 | 9 | 0 | 25 |
| 10 | 1 | 946 | 1 | 5 | 0 | 7 | 11 | 2 | 26 |
| 11 | 6 | 969 | 3 | 6 | 0 | 12 | 11 | 2 | 34 |
| Total | | | 32 | 56 | 1 | 120 | 137 | 17 | 363 |

Due to missing values, only 342 animals could be used for statistical analysis
[1] unknown sex

TABLE XI

Results from SAS' GLM procedure

Dependent Variable: Weight

| Source | DF | Sum of Squares | Mean Square | F Value | Pr > F |
|---|---|---|---|---|---|
| Model | 15 | 10307877.049 | 687191.803 | 39.20 | 0.0001 |
| Error | 326 | 5715510.448 | 17532.241 | | |
| Corrected Total | 341 | 16023387.497 | | | |

| R-Square | C.V. | Root MSE | Weight Mean |
|---|---|---|---|
| 0.64 | 13.3 | 132.4 | 994.5 |

| Source | DF | Type III SS | Mean Square | F Value | Pr > F |
|---|---|---|---|---|---|
| Family | 10 | 564679.9319 | 56467.9932 | 3.22 | 0.0006 |
| Period | 3 | 3186031.5131 | 1062010.5044 | 60.57 | 0.0001 |
| Phenotype | 1 | 5838521.6702 | 5838521.6702 | 333.02 | 0.0001 |
| Sex | 1 | 828696.2176 | 828696.2176 | 47.27 | 0.0001 |

Family $\mu$ + Lsmean

| 853 | 1022.6 g | 858 | 903.2 g |
|---|---|---|---|
| 873 | 888.1 g | 880 | 876.5 g |
| 887 | 891.8 g | 898 | 954.3 g |
| 923 | 939.2 g | 932 | 903.1 g |
| 941 | 924.5 g | 946 | 908.4 g |
| 969 | 907.7 g | | |

Period $\mu$ + Lsmean

| 1. | 982.8 g |
|---|---|
| 2. | 748.4 g |
| 3. | 982.4 g |
| 4. | 966.2 g |

Phenotype $\mu$ + Lsmean

| Dwarf | 766.2 g |
|---|---|
| Non-dwarf | 1073.7 g |

Sex $\mu$ + Lsmean

| Hens | 869.1 g |
|---|---|
| Cocks | 970.8 g |

What is claimed is:

1. A method for detecting alleles of a gene responsible for autosomal dwarfism in chicken comprising hybridizing at least one nucleic acid probe derived from a recombinant nucleic acid associated with autosomal dwarfism in chicken to a sample comprising at least a functional part of said gene or a sequence located in close vicinity to said gene, and wherein said recombinant nucleic acid associated with autosomal dwarfism is located within 6 Mega base pairs of microsatellite marker LEI146.

2. The method of claim 1 wherein said recombinant nucleic acid comprises a functional portion of the HMGI-C gene.

3. The method of claim 2 further comprising detecting that the nucleic acid probe is hybridized to said gene or alleles responsible for autosomal dwarfism.

4. The method of claim 2 wherein the HMGI-C gene comprises an HMGI-C cDNA (SEQ ID NO:1) as shown by FIG. 1.

5. The method of claim 2 wherein the HMGI-C gene comprises an HMBI-C genomic DNA as shown by FIG. 5 (SEQ ID NO:2).

* * * * *